United States Patent
West et al.

(10) Patent No.: US 8,008,345 B2
(45) Date of Patent: Aug. 30, 2011

(54) DERMAL THERAPY USING PHOSPHATE DERIVATIVES OF ELECTRON TRANSFER AGENTS

(75) Inventors: Simon Michael West, Williamstown (AU); Robert J. Verdicchio, Succasunna, NJ (US); David Kannar, Belgrave South (AU); Otto H. Mills, Jr., Doylestown, PA (US)

(73) Assignee: Vital Health Sciences Pty. Ltd., Melbourne (AU)

( * ) Notice: Subject to any disclaimer, the term of this patent is extended or adjusted under 35 U.S.C. 154(b) by 1014 days.

(21) Appl. No.: 10/485,196

(22) PCT Filed: Jul. 26, 2002

(86) PCT No.: PCT/AU02/01003
§ 371 (c)(1),
(2), (4) Date: Aug. 5, 2004

(87) PCT Pub. No.: WO03/011303
PCT Pub. Date: Feb. 13, 2003

(65) Prior Publication Data
US 2004/0253318 A1 Dec. 16, 2004

Related U.S. Application Data

(60) Provisional application No. 60/308,496, filed on Jul. 26, 2002, provisional application No. 60/308,506, filed on Jul. 27, 2001.

(51) Int. Cl.
*A01N 43/16* (2006.01)
*A01N 33/18* (2006.01)
*A01N 33/24* (2006.01)
*A61K 31/355* (2006.01)
*A61K 31/04* (2006.01)

(52) U.S. Cl. ........ 514/458; 514/740; 514/830; 514/859; 514/863; 514/887

(58) Field of Classification Search .................. 424/401; 514/458, 740, 830, 859, 863, 864, 887
See application file for complete search history.

(56) References Cited

U.S. PATENT DOCUMENTS

| | | |
|---|---|---|
| 2,407,823 A | 9/1946 | Fieser |
| 2,667,479 A | 1/1954 | Hoffman et al. |
| 2,913,477 A | 11/1959 | Hirschmann |
| 3,127,434 A | 3/1964 | Andrews |
| 3,212,901 A | 10/1965 | Robeson |
| 4,075,333 A | 2/1978 | Josse |
| 4,141,938 A | 2/1979 | Klose |
| 4,299,906 A | 11/1981 | Liu |
| 4,369,172 A | 1/1983 | Schor et al. |
| 4,444,755 A | 4/1984 | Horrobin |
| 4,603,142 A | 7/1986 | Burger et al. |
| 4,654,373 A | 3/1987 | Bertelli |
| 4,684,520 A | 8/1987 | Bertelli |
| 4,686,211 A | 8/1987 | Hara et al. |
| 4,874,883 A | 10/1989 | Uphues et al. |
| 4,952,495 A | 8/1990 | Belly et al. |
| 5,041,434 A | 8/1991 | Lubkin |
| 5,053,222 A | 10/1991 | Takasu et al. |
| 5,091,848 A | 2/1992 | Kojima |
| 5,094,848 A | 3/1992 | Brixner |
| 5,114,957 A | 5/1992 | Hendler et al. |
| 5,138,084 A | 8/1992 | Casagrande et al. |
| 5,173,304 A | 12/1992 | Lohner et al. |
| 5,374,645 A | 12/1994 | Kurihara-Bergstrom et al. |
| 5,387,579 A * | 2/1995 | Meybeck et al. ............. 514/100 |
| 5,446,070 A | 8/1995 | Mantelle |
| 5,474,891 A | 12/1995 | Murphy |
| 5,474,991 A | 12/1995 | Ogata et al. |
| 5,554,781 A | 9/1996 | Reierson |
| 5,570,504 A | 11/1996 | DiStefano et al. |
| 5,583,105 A | 12/1996 | Kovacs et al. |
| 5,589,504 A | 12/1996 | Dannenberg et al. |
| 5,603,949 A | 2/1997 | Meybeck et al. |
| 5,607,921 A | 3/1997 | Bernard et al. |
| 5,643,597 A | 7/1997 | Meybeck et al. |
| 5,656,618 A * | 8/1997 | Meybeck et al. ............. 514/100 |
| 5,741,518 A | 4/1998 | Ribier et al. |
| 5,759,526 A | 6/1998 | Simonnet et al. |
| 5,776,915 A | 7/1998 | Peterson et al. |
| 5,780,504 A | 7/1998 | Ptchelintsev ................... 514/474 |
| 5,804,168 A * | 9/1998 | Murad ............................ 424/59 |
| 5,804,216 A | 9/1998 | Terren et al. |

(Continued)

FOREIGN PATENT DOCUMENTS

| | | |
|---|---|---|
| CA | 1337992 | 1/1996 |
| CA | 2426852 | 5/2002 |
| CA | 2426885 | 5/2002 |
| EP | 0171009 | 2/1986 |
| EP | 0324387 | 7/1989 |

(Continued)

OTHER PUBLICATIONS

Nakamoto Kenichiro et al., "Tocopherol Derivatives, Intermediates Thereof, and Method for their Preparation and Use," CA, Sep. 11, 2001, XP002968707 Abstract.
Gann, P.H. et al., "Lower prostate cancer risk in men with elevated plasma lycopene levels: results of a prospective analysis," Cancer Res. (1999) 59(6):1225-1230.
Min, J. et al., "Effect of apoptosis induced by different vitamin E homologous analogues in human hepatoma cells (HepG2)," J. Hygiene Res. China (2003) 32(4):343-345.
Visarius, T. et al., "Inhibition of human prostate cancer cell proliferation: vitamin E and lycopene targeted pathways regulating cell cycle progression," FASEB J. (2004) 18(8):C103.
Iimura, N. et al., "Complex formation between cationic surfactants and insoluble drugs," Bull. Chem. Soc. Jpn. (1999) 72:2417-2422.

(Continued)

*Primary Examiner* — San-Ming Hui
*Assistant Examiner* — Paul Zarek
(74) *Attorney, Agent, or Firm* — Michael Best & Friedrich LLP

(57) ABSTRACT

There is provided a method for preventing, alleviating symptoms or treating a skin condition comprising topically administering to the skin of a subject a cosmetic or pharmaceutical topical formulation comprising an effective skin-penetrating amount of one or more phosphate derivatives of one or more electron transfer agents.

44 Claims, No Drawings

U.S. PATENT DOCUMENTS

| | | | |
|---|---|---|---|
| 5,807,542 A | 9/1998 | Challis et al. | |
| 5,807,845 A | 9/1998 | Ogata et al. | |
| 5,885,595 A | 3/1999 | Corey et al. | |
| 5,906,811 A | 5/1999 | Hersh | |
| 5,908,846 A | 6/1999 | Bundgaard et al. | |
| 5,916,915 A | 6/1999 | Hong et al. | |
| 5,928,631 A * | 7/1999 | Lucas et al. | 424/65 |
| 5,952,361 A | 9/1999 | Dias Nahoum | |
| 5,952,373 A * | 9/1999 | Lanzendorfer et al. | 514/456 |
| 5,965,750 A | 10/1999 | Oonishi et al. | |
| 5,981,474 A | 11/1999 | Manning et al. | |
| 6,022,867 A | 2/2000 | Ito et al. | |
| 6,028,105 A * | 2/2000 | Nigra | 514/560 |
| 6,046,181 A | 4/2000 | Oonishi et al. | 514/100 |
| 6,048,891 A | 4/2000 | Wechter | |
| 6,096,326 A * | 8/2000 | Wikholm | 424/401 |
| 6,121,249 A | 9/2000 | Weissman et al. | |
| 6,143,770 A | 11/2000 | Lane et al. | |
| 6,184,247 B1 | 2/2001 | Schneider | 514/474 |
| 6,248,758 B1 | 6/2001 | Klokkers et al. | |
| 6,248,779 B1 | 6/2001 | Shimizu et al. | |
| 6,361,800 B1 | 3/2002 | Cooper et al. | |
| 6,384,043 B1 | 5/2002 | Peyman et al. | |
| 6,403,811 B1 | 6/2002 | West | |
| 6,417,223 B1 | 7/2002 | Sanders et al. | |
| 6,423,742 B1 | 7/2002 | Larson | |
| 6,444,220 B2 | 9/2002 | Wiley | |
| 6,444,234 B1 | 9/2002 | Kirby et al. | |
| 6,479,540 B1 | 11/2002 | Constantinides et al. | |
| 6,485,950 B1 | 11/2002 | Kumar et al. | |
| 6,503,545 B1 | 1/2003 | Perlman et al. | |
| 6,579,995 B1 | 6/2003 | West | |
| 6,599,933 B2 | 7/2003 | Takada et al. | |
| 6,641,847 B1 | 11/2003 | Nawar | |
| 6,645,998 B2 | 11/2003 | Sanders et al. | |
| 6,703,384 B2 | 3/2004 | Sanders et al. | |
| 6,727,280 B2 | 4/2004 | Paiepu et al. | |
| 6,770,672 B1 | 8/2004 | Sanders et al. | |
| 7,074,825 B2 | 7/2006 | Mo et al. | |
| 7,179,486 B1 | 2/2007 | Mulye | |
| 2001/0006659 A1 * | 7/2001 | Koike et al. | 424/400 |
| 2001/0044462 A1 | 11/2001 | Hensley et al. | |
| 2002/0045765 A1 | 4/2002 | Kim et al. | |
| 2002/0127198 A1 | 9/2002 | Rothbard et al. | |
| 2002/0131994 A1 | 9/2002 | Schur et al. | |
| 2002/0132845 A1 | 9/2002 | Miller et al. | |
| 2002/0151467 A1 | 10/2002 | Leung | |
| 2003/0035812 A1 | 2/2003 | Ito et al. | |
| 2003/0109575 A1 | 6/2003 | Lambert et al. | |
| 2003/0157326 A1 | 8/2003 | Vaghefi et al. | |
| 2003/0206972 A1 | 11/2003 | Babish et al. | |
| 2004/0052754 A1 | 3/2004 | West et al. | |
| 2004/0067890 A1 | 4/2004 | Gupta | |
| 2004/0096493 A1 | 5/2004 | West | |
| 2004/0097431 A1 | 5/2004 | Sanders et al. | |
| 2004/0097472 A1 | 5/2004 | West et al. | |
| 2004/0131569 A1 | 7/2004 | Schneider et al. | |
| 2004/0167081 A1 | 8/2004 | Abbruzzese et al. | |
| 2004/0204343 A1 | 10/2004 | Fishman | |
| 2004/0234602 A1 | 11/2004 | Fischer et al. | |
| 2004/0235938 A1 | 11/2004 | Sanders et al. | |
| 2004/0241225 A1 | 12/2004 | West | |
| 2005/0009787 A1 | 1/2005 | West et al. | |
| 2005/0089495 A1 | 4/2005 | West | |
| 2006/0241085 A1 | 10/2006 | West et al. | |
| 2006/0257459 A1 | 11/2006 | West et al. | |
| 2006/0281715 A1 | 12/2006 | West | |
| 2006/0281716 A1 | 12/2006 | West et al. | |
| 2007/0042999 A1 | 2/2007 | West et al. | |
| 2007/0135390 A1 | 6/2007 | West et al. | |
| 2009/0004166 A1 | 1/2009 | West et al. | |
| 2009/0005348 A1 | 1/2009 | Ogru et al. | |
| 2009/0036354 A1 | 2/2009 | Gavin et al. | |
| 2009/0186856 A1 | 7/2009 | West et al. | |
| 2009/0233881 A1 | 9/2009 | West et al. | |
| 2009/0239827 A1 | 9/2009 | Ogru et al. | |
| 2010/0076094 A1 | 3/2010 | West et al. | |
| 2010/0209459 A1 | 8/2010 | West et al. | |
| 2010/0222305 A1 | 9/2010 | West et al. | |
| 2010/0261670 A1 | 10/2010 | West et al. | |
| 2011/0003774 A1 | 1/2011 | West et al. | |

FOREIGN PATENT DOCUMENTS

| | | |
|---|---|---|
| EP | 0338429 | 10/1989 |
| EP | 0430045 | 6/1991 |
| EP | 0430336 | 6/1991 |
| EP | 0436911 | 7/1991 |
| EP | 0565007 | 10/1993 |
| EP | 0574255 | 12/1993 |
| EP | 0617963 | 10/1994 |
| EP | 0641790 | 3/1995 |
| EP | 0643969 | 3/1995 |
| EP | 0661053 | 7/1995 |
| EP | 0669132 | 8/1995 |
| EP | 0669437 | 8/1995 |
| EP | 0674904 | 10/1995 |
| EP | 0680760 | 11/1995 |
| EP | 0681840 | 11/1995 |
| EP | 0684043 | 12/1995 |
| EP | 0699440 | 3/1996 |
| EP | 679399 | 8/1997 |
| EP | 0 826 365 A2 | 3/1998 |
| EP | 0845216 | 6/1998 |
| EP | 0699437 | 12/1998 |
| EP | 0965328 | 12/1999 |
| EP | 0 826 365 A3 | 3/2000 |
| EP | 1000541 | 5/2000 |
| EP | 10223897 | 8/2000 |
| EP | 1053749 | 11/2000 |
| EP | 1264595 | 12/2002 |
| GB | 778142 | 7/1957 |
| GB | 1121683 | 7/1968 |
| GB | 2227662 | 8/1990 |
| JP | 50022535 | 3/1975 |
| JP | 52039013 | 3/1977 |
| JP | 53015381 | 2/1978 |
| JP | 58180410 | 10/1983 |
| JP | 59044375 | 3/1984 |
| JP | 59157091 | 9/1984 |
| JP | 61086940 | 5/1986 |
| JP | 61091137 | 5/1986 |
| JP | 61233631 | 10/1986 |
| JP | 62195393 | 8/1987 |
| JP | 63093791 | 4/1988 |
| JP | 63139972 | 6/1988 |
| JP | 4208209 | 7/1992 |
| JP | 4270212 | 9/1992 |
| JP | 5132700 | 5/1993 |
| JP | 5201858 | 8/1993 |
| JP | 5509296 | 12/1993 |
| JP | 6048962 | 2/1994 |
| JP | 6056699 | 3/1994 |
| JP | 6502422 | 3/1994 |
| JP | 6078214 | 10/1994 |
| JP | 6508820 | 10/1994 |
| JP | 7011291 | 1/1995 |
| JP | 7207298 | 8/1995 |
| JP | 7507318 | 8/1995 |
| JP | 7278587 | 10/1995 |
| JP | 7316170 | 12/1995 |
| JP | 8073338 | 3/1996 |
| JP | 8193089 | 7/1996 |
| JP | 08231564 | 9/1996 |
| JP | 8311085 | 11/1996 |
| JP | 8311489 | 11/1996 |
| JP | 8325594 | 12/1996 |
| JP | 9044375 | 2/1997 |
| JP | 9309813 | 12/1997 |
| JP | 10045783 | 2/1998 |
| JP | 10155429 | 6/1998 |
| JP | 10509451 | 9/1998 |
| JP | 10511677 | 11/1998 |
| JP | 11043436 | 2/1999 |
| JP | 11506419 | 6/1999 |
| JP | 11199424 | 7/1999 |
| JP | 11199465 A * | 7/1999 |
| JP | 2000507557 | 6/2000 |

| | | |
|---|---|---|
| JP | 2000198701 | 7/2000 |
| JP | 2001247585 | 9/2001 |
| JP | 2002080475 | 3/2002 |
| JP | 2002088091 | 3/2002 |
| JP | 2003128531 | 5/2003 |
| NZ | 244549 | 7/1994 |
| SU | 925961 | 5/1982 |
| WO | 91/17987 | 11/1991 |
| WO | WO 92/03122 | 3/1992 |
| WO | WO 92/07544 | 5/1992 |
| WO | WO 92/08459 | 5/1992 |
| WO | WO 92/15289 | 9/1992 |
| WO | WO 9302661 | 2/1993 |
| WO | WO 93/15731 | 8/1993 |
| WO | WO 93/24131 | 12/1993 |
| WO | WO 95/31217 | 11/1995 |
| WO | WO 95/34303 | 12/1995 |
| WO | WO 96/17852 | 6/1996 |
| WO | WO 96/20715 | 7/1996 |
| WO | WO 96/21440 | 7/1996 |
| WO | WO 96/29336 | 9/1996 |
| WO | 97/02803 | 1/1997 |
| WO | WO 97/14705 | 4/1997 |
| WO | WO 97/35591 | 10/1997 |
| WO | WO 99/58555 | 11/1999 |
| WO | WO 00/08033 | 2/2000 |
| WO | WO 00/16772 | 3/2000 |
| WO | WO 00/30620 | 6/2000 |
| WO | WO 00/43380 | 7/2000 |
| WO | 00/44237 | 8/2000 |
| WO | 00/44375 | 8/2000 |
| WO | 00/53728 | 9/2000 |
| WO | WO 00/57876 | 10/2000 |
| WO | WO 00/59475 | 10/2000 |
| WO | WO 00/69865 | 11/2000 |
| WO | WO 00/71094 | 11/2000 |
| WO | WO 00/71125 | 11/2000 |
| WO | 00/74684 | 12/2000 |
| WO | 01/13901 | 3/2001 |
| WO | WO 01/19372 | 3/2001 |
| WO | WO 01/22937 | 4/2001 |
| WO | WO 01/35998 | 5/2001 |
| WO | WO 01/46204 | 6/2001 |
| WO | WO 01/58889 | 8/2001 |
| WO | WO 02/13810 | 2/2002 |
| WO | WO 02/26238 | 4/2002 |
| WO | WO 02/36736 | 5/2002 |
| WO | WO 02/39996 | 5/2002 |
| WO | WO 0240033 | 5/2002 |
| WO | WO 0240034 | 5/2002 |
| WO | WO 03/013550 | 2/2003 |
| WO | WO 03/024429 | 3/2003 |
| WO | WO 03/024430 | 3/2003 |
| WO | WO 03/026673 | 4/2003 |
| WO | WO 03/039461 | 5/2003 |
| WO | WO 03/043570 | 5/2003 |
| WO | WO 03/049774 | 5/2003 |
| WO | WO 03/053407 | 7/2003 |
| WO | 03/068209 | 8/2003 |
| WO | 03/097714 | 11/2003 |
| WO | WO 03/101480 | 12/2003 |
| WO | WO 2004/014432 | 2/2004 |
| WO | WO 2004/060315 | 7/2004 |
| WO | WO 2004/064831 | 8/2004 |
| WO | WO 2004/091636 | 10/2004 |
| WO | WO 2004/092186 | 10/2004 |
| WO | WO 2004/092187 | 10/2004 |
| WO | WO 2005/023282 | 3/2005 |
| WO | WO 2005/084678 | 9/2005 |
| WO | WO 2006/012692 | 2/2006 |
| WO | WO 2006/092024 | 9/2006 |
| WO | WO 2006/092025 | 9/2006 |
| WO | WO 2006/133506 | 12/2006 |
| WO | WO 2007/070981 | 6/2007 |

OTHER PUBLICATIONS

Imada, I. et al., "Photochemical reaction of ubiquinone. IV. Coenzymatic activity of ubiquinone and related compounds," Chem. Pharm. Bull. (1965) 13:136-142.

Aberg, F. et al., "Distribution and redox state of ubiquinones in rat and human tissues," Arch. Biochem. Biophys. (1992) 295(2):230-234.

Almeida, M.E.M. et al., "Evaluation of soybean oil deodorization distillate for Vitamin E recovery," Arq. Biol. Tecnol. (1994) 37(4):1003-1011.

Barrett, C.W. et al., "The effect of particle size and vehicle on the percutaneous absorption of fluocinolone acetonide," Brit. J. Dermatol. (1965) 77:576-578.

Bikerman, J.J., "Mechanical destruction of young and old foam films," J. Phys. Chem. (1952) 56:164-165.

Blom, J.H. et al., "Reproductive success of female rainbow trout (*Oncorhynchus mykiss*) in response to graded dietary ascorbyl monophosphate levels," Biol. of Reproduction (1995) 52:1073-1080.

Cevc, G. "Transdermal drug delivery of insulin with ultradeformable carriers," Clin. Pharmacokinet. (2003) 42(5):461-474.

Cevc, G. et al., "Ultraflexible vesicles, transfersomes, have an extremely low pore penetration resistance and transport therapeutic amounts of insulin across the intact mammalian skin," Biochim. Biophys. Acta (1998) 1368:201-215.

De Wolfe, F.A. et al., "Ligand-binding proteins: their potential for application in systems for controlled delivery and uptake of ligands," Pharmacol. Rev. (2000) 52(2):207-236.

Devaraj, S. et al., "Modulation of monocyte-macrophage function with alpha-tocopherol: implications for atherosclerosis," Nat. Rev. (2002) 60(1):8-14.

Devaraj, S. et al., "Alpha tocopherol supplementation decreases serum C-reactive protein and monocyte interleukin-6 levels in normal volunteers and type 2 diabetic patients," Free Radic. Biol. Med. (2000) 29(8):790-792.

Ernster, L. et al., "Biochemical, physiological and medical aspects of ubiquinone function," Biochim. Biophys. Acta (1995) 1271:195-204.

Octoplus, "Formulation Development of Poorly Soluble Drugs" (www.octoplus.nl) (1999) 2 pages (downloaded Nov. 2008).

Fracalossi, D.M. et al., "Oscars, *Astronotus ocellatus*, have a dietary requirement for vitamin C," J. Nutrition (1998) 128:1745-1751.

Frei, B. et al., "Ubiquinol-10 is an effective lipid-soluble antioxidant at physiological concentrations," Proc. Natl. Acad. Sci. (1990) 87:4879-4883.

Godin, B. et al., "Ethosomes: new prospects in transdermal delivery," Crit. Rev. Thera. Drug Car. Syst. (2003) 20(1):63-102.

Goff et al., "Prevention of cardiovascular disease in persons with Type 2 diabetes mellitus: current knowledge and rationale for the action to control cardiovascular risk in diabetes (ACCORD) trial," Am. J. Cardiol. (2007) 99(suppl):4i-20i.

Griffin, E. et al., "A link between diabetes and atherosclerosis: glucose regulates expression of CD36 at the level of translation," Nature Med. (2001) 7(7):840-846.

Guo, J. et al., "Transdermal delivery of insulin in mice by using Lecithin vesicles as a carrier," Drug Del. (2000) 7:113-116.

Heron-Milhavet, L. et al., "Muscle-specific overexpression of CD36 reverses the insulin resistance and diabetes of MKR mice," Endocrinology (2004) 145:4667-4676.

Kagan, V. et al., "Antioxidant effects of ubiquinones in microsomes and mitochondria are mediated by tocopherol recycling," Biochem. Biophys. Res. Commun. (1990) 169(3):851-857.

Karrer, V.P. et al., "d,1-alpha-tocopherol-phosphorsaure-ester," Zurich, Chemisches Institut der Universitat (1933) p. 1137-1138, in German.

King, M.J. et al., "Transdermal delivery of insulin from a novel biphasic lipid system in diabetic rats," Diab. Tech. Therap. (2002) 4(4):479-488.

Knowler, W.C. et al., "Preventing Non-insulin-dependent diabetes," Diabetes (1995) 44:483-488.

Langsjoen, P.H. et al., "Overview of the use of CoQ10 in cardiovascular diseases," Biofactors (1999) 9:273-284.

Lass, A. et al., "Electron transport-linked ubiquinone-dependent recycling of α-tocopherol inhibits autooxidation of mitochondrial membranes," Arch. Biochem. Biophys. (1998) 352(2):229-236.

Lee, C-F. et al., "Attenuation of UV-induced apoptosis by coenzyme Q10 in human cells harboring large-scale deltion of mitochontrial DNA," Ann. N. Y. Acad. Sci. (2005) 1042:429-438.

Lei, B. et al.,.. Progress in alpha-tocopherol preparation technology, Xiandai Huagong (1997) 17(7):13-15.

Maguire, J.J. et al., "Succinate-ubiquinone reductase linked recycling of alpha-tocopherol in reconstituted systems and mitochondria: requirement for reduced ubiquinone," Arch. Biochem. Biophys. (1992) 292(1):47-53.

Mellors, A. et al., "The inhibition of mitochondrial peroxidation by ubiquinone and ubiquinol," J. Biol. Chem. (1966) 241(19):4353-4356.

Merck Index, The, "α-estradiol" Thirteenth Edition, Whitehouse Station, NJ (2001) p. 660.

Merck Index, The, "Fludarabine to Fludeoxyglucose F18" pages, Thirteenth Edition, Whitehouse Station, NJ (2001) pp. 729-730.

Miyamoto, S. et al., "Synthesis of a novel phosphate ester of a vitamin E derivative and its antioxidative activity," Biosci. Biotech. Biochem. (1998) 62(12):2463-2466.

Morgan, T.M. et al., "Transdermal delivery of estradiol in postmenopausal women with a novel topical aerosol," J. Pharm. Sci. (1998) 87(10):1226-1228.

Morgan, T.M. et al., "Enhanced transdermal delivery of sex hormones in swine with a novel topical aerosol," J. Pharm. Sci. (1998) 87(10):1219-1225.

Mortensen, S.A., "Perspectives on therapy of cardiovascular diseases with coenzyme Q10 (ubiquinone)," Clin. Investig. (1993) 71(Suppl. 8):S116-S123.

Munteanu, A. et al., "Modulation of cell proliferation and gene expression by alpha-tocopheryl phosphates: relevance to atherosclerosis and inflammation," Biochem. Biophys. Res. Comm. (2004) 318(1):311-316.

Ostrenga, J. et al., "Significance of vehicle composition I: Relationship between topical vehicle composition, skin penetrability, and clinical efficacy," J. Pharm. Sci. (1971) 60(8):1175-1179.

Owens, D.R. et al., "Alternative routes of insulin delivery," Diabet. Med. (2003) 20:886-898.

Parker et al., "Neonatal vitamin K administration and childhood cancer in the North of England: retrospective case-control study," BMJ (1998) 316:189-193.

Potts, R.O. et al., "Predicting skin permeability," Pharm. Res. (1992) 9(5):663-669.

Puratchikody, A. et al., "Reverse phase—high performance liquid chromatographic determination of atorvastatin calcium in solid dosage forms," Pharma. Review (2003) 1(2):79-80, 83—STN File CA, Abstract 139:399976 only.

Sevast'Ianov, V.I. et al., "Transdermal delivery of insulin," Meditsinskaia Tekhnika (2003) 2:21-24.

Seyama, Y. et al., "Comparative effects of Vitamin K2 and estradiol on experiemental arteriosclerosis with diabetes mellitus," Int. J. Vitam. Nutr. Res. (2000) 70(6):301-304, Abstract only.

Singh, R.B. et al., "Randomized double-blind placebo-controlled trial of coenzyme Q10 in patients with acute myocardial infarction," Cardiov. Drugs Ther. (1998) 12:347-353.

Stedman's Medical Dictionary, "Tocopherol," "Tocotrienol," and "Vitamin K1", 22nd Edition, Williams & Wilkins Co. (1972) p. 1303 and 1400.

Younis et al., "The prevention of type 2 diabetes mellitus: recent advances," Q.J. Med. (2004) 97:451-455.

Gianello, R. et al., "α-tocopheryl phosphate: a novel, natural form of vitamin E," Free Radical Biol. Med. (2005) 39:970-976.

Negis, Y. et al., "On the existence of cellular tocopheryl phosphate, its synthesis, degradation and cellular roles: a hypothesis," IUBMB Life (2005) 57(1):23-25.

Ogru, E. et al., "Vitamin E phosphate: an endogenous form of vitamin E," Medimond S.r.l. (2003) 127-132.

Traber, M.G. et al., "Human plasma vitamin E kinetics demonstrates rapid recycling of plasma RRR-alpha-tocophero," Proc. Natl. Acad. Sci. USA (1994) 91:10005-10008.

United States Office Action for U.S. Appl. No. 09/979,436 dated Apr. 4, 2002 (6 pages).

United States Office Action for U.S. Appl. No. 09/979,436 dated Sep. 23, 2002 (6 pages).

United States Office Action for U.S. Appl. No. 10/416,775 dated Nov. 2, 2005 (10 pages).

United States Office Action for U.S. Appl. No. 10/416,775 dated Jun. 12, 2006 (10 pages).

United States Office Action for U.S. Appl. No. 10/416,775 dated Jul. 12, 2007 (11 pages).

United States Office Action for U.S. Appl. No. 10/416,775 dated Dec. 17, 2008 (6 pages).

United States Office Action for U.S. Appl. No. 10/416,774 dated Sep. 6, 2007 (9 pages).

United States Office Action for U.S. Appl. No. 10/416,774 dated Jun. 11, 2008 (15 pages).

United States Office Action for U.S. Appl. No. 10/416,774 dated Feb. 17, 2009 (15 pages).

United States Office Action for U.S. Appl. No. 10/416,774 dated Apr. 15, 2009 (14 pages).

United States Office Action for U.S. Appl. No. 10/462,480 dated Dec. 1, 2006 (10 pages).

United States Office Action for U.S. Appl. No. 10/462,480 dated Nov. 1, 2007 (10 pages).

United States Office Action for U.S. Appl. No. 10/462,480 dated Feb. 20, 2009 (17 pages).

United States Office Action for U.S. Appl. No. 10/486,142 dated Mar. 18, 2008 (12 pages).

United States Office Action for U.S. Appl. No. 10/487,743 dated Dec. 2, 2005 (22 pages).

United States Office Action for U.S. Appl. No. 10/487,743 dated Jul. 27, 2006 (23 pages).

United States Office Action for U.S. Appl. No. 10/498,684 dated Oct. 2, 2008 (21 pages).

United States Office Action for U.S. Appl. No. 10/498,684 dated Jun. 23, 2009 (19 pages).

United States Office Action for U.S. Appl. No. 10/524,090 dated Mar. 12, 2008 (12 pages).

United States Office Action for U.S. Appl. No. 10/542,511 dated Aug. 8, 2007 (19 pages).

United States Office Action for U.S. Appl. No. 10/542,511 dated Mar. 31, 2008 (20 pages).

United States Office Action for U.S. Appl. No. 10/542,511 dated Feb. 5, 2009 (23 pages).

United States Office Action for U.S. Appl. No. 10/551,200 dated Jan. 28, 2009 (11 pages).

United States Office Action for U.S. Appl. No. 10/551,201 dated Jan. 24, 2008 (6 pages).

United States Office Action for U.S. Appl. No. 10/551,203 dated Dec. 6, 2006 (13 pages).

United States Office Action for U.S. Appl. No. 10/551,203 dated Sep. 7, 2007 (13 pages).

United States Office Action for U.S. Appl. No. 10/551,203 dated Apr. 11, 2008 (11 pages).

United States Office Action for U.S. Appl. No. 10/551,203 dated Dec. 19, 2008 (13 pages).

United States Office Action for U.S. Appl. No. 10/551,203 dated Jul. 21, 2009 (21 pages).

United States Patent Office Action for U.S. Appl. No. 11/817,453 dated Oct. 9, 2009 (11 pages).

United States Patent Office Action for U.S. Appl. No. 10/462,480 dated Nov. 27, 2009 (9 pages).

Nakayama, S. et al., "Protective effects of a stable, water-soluble vitamin E on photodamage induced by UVB irradiation in cultured mouse skin," Photomedicine and Photobiology (1998) 20:99-100.

United States Patent Office Action for U.S. Appl. No. 10/416,774 dated Dec. 18, 2009 (11 pages).

United States Patent Office Action for U.S. Appl. No. 10/542,511 dated Jan. 12, 2010 (13 pages).

Japanese Patent Office Action for Application No. 2003-516533 with a mailing date of Oct. 20, 2009 (3 pages).

Suzuki, T. et al., "The solution behavior and the association structure of long-chain monoalkyl phosphates," Chem. Soc. Japan (1986) 633-640 with English abstract.

United States Patent Office Action for U.S. Appl. No. 11/917,831 dated Jan. 19, 2011 (10 pages).

Devaraj, S. et al., "Alpha tocopherol decreases CD36 expression in human monocyte-derived macrophages," J. Lipid Res. (2001) 42:521-527.

Gianello, R. et al., "Subchronic oral toxicity study of mixed tocopheryl phosphates in rats," Int. J. Toxicol. (2007) 26:475-490.

Libinaki, R. et al., Evaluation of the safety of mixed tocopheryl phosphates (MTP)-a formulation of alpha-tocopheryl phosphate plus alpha-di-tocopheryl phosphate, Food Chem. Toxicol. (2006) 44(7):916-932.

Little, P.J. et al., "Phosphorylated troglitazone activates PPARγ and inhibits vascular smooth muscle cell proliferation and proteoglycan synthesis," J. Cardiovasc. Pharmacol. (2008) 51(3):274-279.

Mukherjee, S. et al., "Cardioprotection with α-tocopheryl phosphate: amelioration of myocardial ischemia reperfusion injury is linked with its ability to generate a survival signal through Akt activation," Biochim. Biophys. Acta (2008) 1782:498-503.

Negis, Y. et al., "Molecular mechanism of alpha-tocopheryl-phospate transport across the cell membrane," Biochem. Biophys. Res. Comm. (2007) 359:348-353.

Negis, Y. et al., "The effect of tocopheryl phosphates on atherosclerosis progression in rabbits fed with a high cholesterol diet," Arch. Biochem. Biophys. (2006) 450:63-66.

Rerek, M.E. et al., "Disodium lauriminodipropionate tocopheryl phosphates: a potent new anti-inflammatory," Cosmetics & Toiletries magazine (2003) 118(7):63-67.

Rezk, B.M. et al., "The extraordinary antioxidant activity of vitamin E phosphate," Biochim. Biophys. Acta (2004) 1683:16-21.

Ricciarelli, R. et al., "Vitamin E reduces the uptake of oxidized LDL by inhibiting CD36 scavenger receptor expression in cultured aortic smooth muscle cells," Circulation (2000) 102:82-87.

Teupser, D. et al., "Alpha-tocopherol down-regulates scavenger receptor activity in macrophages," Atherosclerosis (1999) 144:109-115.

United States Patent Office Action for U.S. Appl. No. 12/212,803 dated Mar. 12, 2010 (13 pages).

United States Patent Office Action for U.S. Appl. No. 10/498,684 dated Jul. 7, 2010 (21 pages).

United States Patent Office Action for U.S. Appl. No. 10/524,090 dated Mar. 3, 2010 (18 pages).

United States Patent Office Advisory Action for U.S. Appl. No. 10/542,511 dated May 25, 2010 (3 pages).

United States Patent Office Action for U.S. Appl. No. 11/817,453 dated Aug. 2, 2010 (10 pages).

United States Patent Office Action for U.S. Appl. No. 12/158,932 dated Aug. 19, 2010 (15 pages).

Brandt, M., "Steroid hormone biosynthesis," (2002) printed from http://www.rose_hulman.edu/~brandt/Chem430/ Steroids.pdf on Nov. 20, 2010 (7 pages).

Jiang, Q. et al., "γ-tocopherol, the major form of vitamin E in the U.S. diet, deserves more attention," Am. J. Clin. Nutri. (2001) 74(6):714-722.

United States Patent Office Action for U.S. Appl. No. 10/524,090 dated Nov. 23, 2010 (19 pages).

United States Patent Office Action for U.S. Appl. No. 11/817,439 dated Nov. 24, 2010 (15 pages).

United States Patent Office Action for U.S. Appl. No. 12/628,443 dated Feb. 18, 2011 (15 pages).

Schwenke, D.C. et al., "α-tocopherol protects against diet induced atherosclerosis in New Zealand white rabbits," J. Lipid Res. (2002) 43:1927-1938.

United States Patent Office Action for U.S. Appl. No. 12/834,553 dated Apr. 14, 2011 (13 pages).

United States Patent Office Action for U.S. Appl. No. 11/817,453 dated Mar. 9, 2011 (12 pages).

United States Patent Office Action for U.S. Appl. No. 11/817,439 dated May 11, 2011 (11 pages).

* cited by examiner

DERMAL THERAPY USING PHOSPHATE DERIVATIVES OF ELECTRON TRANSFER AGENTS

CROSS-REFERENCE TO RELATED APPLICATIONS

This application is a national stage filing under 35 U.S.C. 371 of International Application No. PCT/AU02/01003, filed on Jul. 26, 2002, which claims priority to U.S. Provisional Application No. 60/308,496, filed on Jul. 27, 2001, and to U.S. Provisional Application No. 60/308,506, filed on Jul. 27, 2001.

FIELD OF THE INVENTION

This invention relates to a method for treating preventing, alleviating symptoms or treating a skin condition using topical formulations.

BACKGROUND OF THE INVENTION

Skin Health

The skin is the largest organ of the body, and, among other things, functions to protect the internal organs from external chemical, physical and pathological hazards. Normal skin is composed of an outer epidermis covering sub dermal layers, where each layer comprises different sections. The outer cornified layer of the epidermis possesses properties of strength, flexibility, high electrical impedance and dryness that retards penetration and proliferation of microorganisms. The cornified protective layer is formed by the migration of maturing keratinocytes that are formed at the junction of the dermis and epidermis.

Vitamin E (tocopherol) is an essential part of skin metabolism and is known to be important for skin health, with deficiency manifesting as a cornified, scaly delicate skin, thickened epidermis, scaling, lesions, chronic infection, inflammation and erythema. Vitamin E is the main naturally occurring lipid soluble agent protecting the skin from stress, and is the main lipid soluble agent protecting the cell membrane lipids from peroxidation.

Skin is subject to constant stress due to exposure to everyday elements—sun, wind and water. As a result, it is common for many cosmetic products such as lotions, moisturizers, shampoo and conditioners to contain vitamin E to assist in maintaining skin health. In order to assist in maintaining skin health, it is necessary for the vitamin E to reach the target area. The most direct method of achieving this targeting is to apply a topical formulation to the affected area. However, topical application of vitamin E to the skin using current formulations has variable success due to the skin's ability to erect an impenetrable barrier to many outside elements. It is important to provide for the penetration of vitamin E through the stratum corneum to the other parts of the epidermis and to the dermis.

It is believed that topical formulations using tocopherol acetate have not been able to deliver adequate tocopherol for the epidermal and dermal layers, and therefore provide little benefit. As tocopheryl acetate is a lipidic material requiring formulation with an oil in water emulsion, absorption from such a formulation is inadequate.

Skin Damage

The skin is susceptible to damage by bacteria, trauma, aging, free radicals, physical stress and chemical agents. The symptoms resulting from this damage include inflammation, erythema, swelling, photo-aging, thickening of the epidermis, acne, and wrinkling.

In response to stress, a variety of systems in the skin are believed to be activated and are also believed to regulate skin thickness. Cells in the epidermal-dermal junction maintain epidermal thickness. The nucleus of these cells controls the response to stress. When trauma occurs, oxygen permeates the epidermis and dermis and produces free radicals. It is thought that when epidermis is removed or damaged allowing increased oxygen permeation, protective mechanisms generate new epidermis. Such mechanisms are believed to involve phosphorylation of proteins generated when the oxygen concentration rises at the dermis/epidermis boundary. There is some evidence that tocopheryl phosphate is associated with proteins that are phosphorylated and become messengers that interact with the inflammatory response.

Many skin diseases involve inflammation and increased conversion of dermis to epidermis. When cells are damaged by free radicals, physical stress or chemical agents, the injury sets off a defensive inflammatory response typically characterized by four fundamental symptoms; redness, pain, heat and swelling. The inflammatory response has protective and defensive roles that serve to remove harmful microbes, toxins or foreign materials at the site of injury and restore tissue homeostasis. Within minutes of sustaining an injury there is noticeable vasodilabon with associated redness or wheal. Blood flow is improved to the damaged tissue and thereby increases available inflammatory mediators responsible for release of inflammatory immuno-modulators such as leukocytes that contribute significantly to the persistence of inflammation. During this process, the level of free radicals, pathogens and foreign bodies increases causing production of prostaglandin $E_2$ synthesized from arachadonic acid by peroxidation. This in turn suppresses the production of interleukin 2 increasing vasodilation observed as redness or erythema.

One example of a skin condition involving epidermal thickening is scleroderma. Treatment of scleroderma primarily deals with reducing symptoms such as epidermal thickening, and involves the administration of corticosteroids, penicillamine, colchicine and various immunosuppresive drugs. Drugs used to reduce thickened epidermis associated with scleroderma often need to be used on a chronic basis and are associated with side effects. For example, colchicine is associated with gastrointestinal upset and nausea, corticosteroids is associated with fluid, electrolyte, musculoskeletal, gastrointestinal, dermatological, neurological, endocrine, ophthalmic, metabolic and psychiatric disturbances, and penicillamine is associated with renal and hepatic toxicity, hematological disturbances, gastrointestinal upset, taste changes, iron deficiency, muscular disorders, skin friability, and optical changes.

Acne

Acne vulgaris is a common inflammatory disorder of specialized follicles located exclusively on the face, chest and back, resulting in disfiguring and obstructive inflammatory lesions, scars or cysts. It is more typically known as acne and affects over 85% of adolescents and young adults. Although not clearly defined, it is basically understood that hormones, excess seburn and bacteria (*Propionibacterium* acnes) unite in susceptible individuals to obstruct skin follicles and lead to inflammatory processes that manifest clinically as erythematous papules, pustules or nodules. Initially, obstruction within the follicle is clinically undetectable and called microcomedones. As comedones enlarge they become clearly apparent as blackheads (open comedones) or whiteheads (closed comedones). These comedones may rupture to form erythematous papules, pustules or nodules that can develop pitted scars or mocules as the inflammation resolves.

The typical acne cycle may be described as follows: (i) increased seburn production in pilosebaceous glands; (ii) hyperkeratinization resulting in coalescence of keratinocytes in a follicle forming a plug; (iii) colonization of microorganisms produces antigens and inflammation; (iv) lipid oxidation/hydrolysis produces free radicals and increased fatty acids, which further increases inflammation due to chemo tactic responses, which promote polymorphonuclear leucocytes; (v) buildup within the follicle of keratin and seburn causes the follicle to rupture into the epidermis and dermis, as the microscopic orifice is too small for the material to discharge from the skin surface; and (vi) release of keratin and seburn into layers of the epidermis and dermis produce highly inflamed papules as described above.

Reported Developments

Compounds such as vitamins E, A, C and K, tocotrienol, and ubiquinone are reputed valuable agents as supportive therapy in managing skin conditions. It has been established that vitamin E stabilizes lysosomes, interacts with eicosanoids to reduce prostaglandin $E_2$ synthesis and increases interleukin 2 production resulting in anti-inflammatory and immunostmulating effects. Interleukin 2 (IL-2) production is known to increase mitosis and cytokines including activated T cells, thereby augmenting a rapid immune response to a particular antigen. This phenomenon is measurable within 48 to 72 hours after initiation and the likely source of the clinical benefits noted for vitamin E. These effects require adequate levels of vitamin E in an appropriate form, to be delivered to dermal layers to produce the required benefit.

For many dermatological conditions, Vitamin E therapy has however not been substantiated by human studies. Effective delivery of tocopherol and other poorly absorbed or soluble compounds required to initiate a beneficial effect can be difficult to achieve and delivery of any reproducible benefit requires accumulation of an effective concentration of the compound. Further, vitamin E has even been associated with local adverse reactions including papular and follicular dermatitis. Topical and oral application of the Vitamin E acetate derivative, tocopheryl acetate, has provided inconsistent results for the treatment and/or prevention of UV damage, skin cancer formation, immunosuppression in animals, the associated erythema, edema and skin sensitivity of sunburn, skin roughness, length of facial lines, wrinkle depth and wound healing.

Acne treatments presently available for use are designed to inhibit one or more of the following factors, namely, (i) increased seburn, (ii) hyperkeratinization, and (iii) inflammation and inhibition of microorganisms. Examples of current active ingredients are the oxidant, benzoyl peroxide (antimicrobial), retinoids (reduction in keratinization by promoting cell turnover, normalizing keratinization of the pilosebaceous follicle, preventing obstruction, indirectly reducing inflammatory lesions and comedogenesis.), azelaic acid (inhibits keratinization, promotes cell turn-over and is mildly effective against microorganisms), salicylic acid (antimicrobial, seburn reducer and anti keratolytic) and sulfur. Current acne treatments commonly involve use of topical preparations of these agents as well as systemic antibiotics. These preparations have an antibacterial effect and reduce inflammation.

Exemplary antibiotics incorporated in compositions includes the lincomycin family, erythromycin and tetracycline. Acne treatment compositions containing benzoyl peroxide are also known. Antibiotic-containing compositions are known which also include anti-inflammatory steroids.

Attempts to improve the effectiveness of topical antibiotic compositions for use in the treatment of acne have taken a number of approaches. One approach is the use of skin-penetrating vehicle compositions that reportedly increase the skin's absorption of a physiologically active substance, including antibiotics. However, not all penetrating agents in combination with antibiotics are effective for the treatment of acne. For example, the use of a skin-penetrating vehicle results in an effective anti-acne composition with erythromycin but not with tetracycline. A further approach relates to the use of a composition containing two different active agents, such as erythromycin and Vitamin A acid or benzoyl peroxide.

The reported topical anti-acne methods and compositions exhibit the disadvantages of limited effectiveness and frequent excessive adverse skin reactions. These treatments all have their drawbacks. For example, when benzoyl peroxide (a source of free radicals) is applied in acne treatment, scaliness results, indicating that free radicals may cause additional epidermal stress.

Sun Damage

Exposure to ultraviolet light and environmental stress and their combined detrimental effects of skin and even hair have been known for some time. Environmental stress in combination with UV light produces free radicals which are potent highly reactive peroxidase toxins which damage tissue cells leading to considerable skin conditions such as carcinogenesis and photoaging. Current knowledge in the areas of photobiology and photodermatology show that protection against the effects of UV light (in the range of 290-400 nm) is crucial to avoid the effects of sunburn, pigmentation, photoaging (solar elastosis), solar keratosis, skin cancers (melanoma and carcinoma) as well as immuno-suppression.

The common use of broad-spectrum sunscreens which absorb UV light in the range of 290-400 nm is reflected in the myriad of products available in the marketplace. Although many formulators have included tocopherol as the acetate ester, it is not known how the acetate group is removed to allow the free tocopherol to become involved in skin metabolism. It is known that free tocopherol may be inflammatory and it has been found that poor dietary intake of tocopherol leads to sun-sensitive skin.

New Products

In our co-pending international patent application no PCT/AU01/01476 we disclose a composition comprising the reaction product of:
(a) one or more phosphate derivatives of one or more hydroxylated actives; and
(b) one or more complexing agents selected from the group consisting of amphoteric surfactants, cationic surfactants, amino acids having nitrogen functional groups and proteins rich in these amino acids.

The hydroxylated actives include the sub-group of electron transfer agents. The content of PCT/AU01/01476 is referred to and incorporated herein.

SUMMARY OF THE INVENTION

The present invention relates to our surprising finding that phosphate derivatives of electron transfer agents have properties which can prevent, alleviate the symptoms of, or treat a skin condition using benign compounds.

According to a first aspect of the invention, there is provided a method for preventing, alleviating symptoms or treating a skin condition, the method comprising topically administering to the skin of a subject a cosmetic or pharmaceutical topical formulation comprising an effective skin-penetrating amount of one or more phosphate derivatives of one or more electron transfer agents.

Typically, the topical formulation further comprises a topically acceptable carrier.

The term "skin conditions" is used herein to refer to disturbances in or injury to the structure, functioning and/or appearance of the skin, such disturbances may be mediated by oxidative or free radical sources. Such disturbances or injuries are typically manifested as various symptoms including but not limited to epidermal thickening, erythema, inflammation, comedone formation, scaling, heat, swelling, pain and excess sebum production. The skin conditions include deterioration of skin homeostasis, inflammation, erythema, wound, burn, sun sensitivity, dandruff, rosacea, dermatitis, gingivitis, sunburn, heat burn, psoriasis, insect bites, seborrheic dermatitis, calluses, corns, eczema, photo-aging, wrinkles, common warts, plantar warts, thickening of the epidermal layer and pigmentation.

Such treatments may be effective alone or may be used with other active compounds such as antibiotics, antiseptics, antihistamines, disinfectants, anti-inflammatories, keratolytic agents and sunscreens. One example of a suitable disinfectant is tea tree oil.

The skin for which this method may be used includes the skin of humans and animals with similar skin types to humans, such as mammals. Under some situations, it may be useful to shave animal skin prior to use of the method according to the present invention to improve efficacy.

The term "electron transfer agent" is used herein to refer to the class of chemicals which may be phosphorylated and which (in the non-phosphorylated form) can accept an electron to generate a relatively stable molecular radical or accept two electrons to allow the compound to participate in a reversible redox system. Examples of classes of electron transfer agent compounds that may be phosphorylated include hydroxy chromans including alpha, beta and gamma tocols and tocotrienols in enantiomeric and raecemic forms; quinols being the reduced forms of vitamin K1 and ubiquinone; hydroxy carotenoids including retinol; calciferol and ascorbic acid.

The term "hydroxy chroman" is used herein to refer to a class of compounds including a core dihydrobenzo-γ-pyran bicyclic ring structure. The preferred hydroxy chromans include an isoprenoid side chain covalently bonded to the pyranyl carbon alpha to the pyranyl oxygen. The most preferred members of the isoprenoid dihydropyran class of compounds include the tocopherols, all of which include a hydroxyl group para to the pyranyl oxygen, and differ in their methyl substitution pattern about the fused benzo ring. These forms are referred to as the alpha, beta, gamma and delta forms of tocopherol. Other related compounds include the tocotrienols.

The term "phosphate derivatives of electron transfer agents" comprises compounds covalently bound by means of an oxygen to the phosphorus atom of a phosphate group thus forming a carbon-oxygen-phosphorous bond. The oxygen atom is typically derived from a hydroxyl group on the electron transfer agents. The phosphate derivative may exist in the form of a free phosphoric acid, a salt thereof, a di-phosphate ester thereby including two molecules of electron transfer agent, a mixed ester including two different compounds selected from electron transfer agents, a phosphatidyl compound wherein the free phosphate oxygen forms a bond with an alkyl or substituted alkyl group and complexes with amphoteric surfactants, cationic surfactants, amino acids having nitrogen functional groups and proteins rich in these amino acids.

For example, tocopheryl phosphate may be provided mixed with ascorbyl phosphate or as an ascorbyl/tocopheryl phosphate. Similarly, ascorbyl phosphates may be combined with tocotrienol phosphates and/or ubiquinol phosphates. Similarly, retinyl phosphate could be combined with tocopheryl phosphates and/or ascorbyl phosphates. Phosphorylation may be accomplished by any suitable method. Preferably, the hydroxyl group-containing electron transfer agent is phosphorylated using $P_4O_{10}$ according to the method in international patent application no PCT/AU00/00452. Excess diphosphate derivatives may be hydrolyzed using methods known to those skilled in the art.

The preferred phosphate derivatives of electron transfer agents which may be used in method of the invention include:
(a) tocopheryl phosphates;
(b) ascorbyl phosphates;
(c) P:tocopheryl P:ascorbyl phosphate diester,
(d) ubiquinyl phosphates;
(e) tocotrienol phosphates;
(f) retinyl phosphates; and
(g) mixtures thereof.

It has further been found that the reaction products of one or more phosphate derivatives of electron transfer agents and one or more complexing agents selected from the group consisting of amphoteric surfactants, cationic surfactants, amino acids having nitrogen functional groups and proteins rich in these amino acids are preferred for reducing deterioration of skin homeostasis or alleviating or treating skin conditions.

Preferably, the topical formulation comprises about 0.01 to 30% by weight of the total composition of one or more complexes of one or more phosphate derivatives of one or more electron transfer agents. The formulation may comprise about 1 to 15%, about 1 to 5%, or about 1 to 3% by weight of the total composition of one or more complexes of one or more phosphate derivatives of one or more electron transfer agents. It will be appreciated that the amount of the one or more complexes of one or more phosphate derivatives of one or more electron transfer agents in a given formulation will can vary depending on the skin condition, the area of and type of skin to be treated, and the type or composition of the formulation.

According to a second aspect of the invention, there is provided a method for preventing, alleviating symptoms or treating a skin condition, the method comprising topically administering to the skin of a subject a cosmetic or pharmaceutical topical formulation comprising an effective skin-penetrating amount of one or more complexes of one or more phosphate derivatives of one or more electron transfer agents.

Typically, the topical formulation further comprises a topically acceptable carrier.

The term "complexes of phosphate derivatives of one or more electron transfer agents" refers to the reaction product of one or more phosphate derivatives of one or more electron transfer agents and one or more complexing agents selected from the group consisting of amphoteric surfactants, cationic surfactants, amino acids having nitrogen functional groups and proteins rich in these amino acids as disclosed in international patent application no PCT/AU01/01476.

The preferred complexes of phosphate derivatives of one or more electron transfer agents which may be used in the method of the invention include the reaction products of a phosphate of an electron transfer agent selected from the group consisting of ascorbyl phosphates, retinyl phosphates, tocopheryl phosphates, tocotrienol phosphates and P:tocopheryl P:ascorbyl phosphate diesters; ubiquinyl phosphates or mixtures thereof with a complexing agent selected from the group consisting of arginine, histadine and tertiary substituted amines, such as those according to the following formula:

$NR^1R^2R^3$ wherein $R^1$ is chosen from the group comprising straight or branched chain mixed alkyl radicals from C6 to C22 and carbonyl derivatives thereof;

$R^2$ and $R^3$ are chosen independently from the group comprising H, $CH_2COOX$, $CH_2CHOHCH_2SO_3X$, $CH_2CHOHCH_2OPO_3X$, $CH_2CH_2COOX$, $CH_2COOX$, $CH_2CH_2CHOHCH_2SO_3X$ or $CH_2CH_2CHOHCH_2OPO_3X$ and X is H, Na, K or alkanolamine provided $R^2$ and $R^3$ are not both H; and wherein when $R^1$ is RCO then $R^2$ may be $CH_3$ and $R^3$ may be $(CH_2CH_2)N(C_2H_4OH)$—$H_2CHOPO_3$ or $R^2$ and $R^3$ together may be $N(CH_2)_2N(C_2H_4OH)CH_2COO$—.

Examples of such complexes of phosphate derivatives of one or more electron transfer agents are lauryliminodipropionic acid tocopheryl phosphates, ubiquinyl phosphate arginine complexes and retinyl phosphate histadine complexes.

The term "effective skin-penetrating amount" is used herein to refer to an amount that penetrates the stratum corneum to reach the epidermal and dermal layers of the skin in an amount that is measurably effective in the reduction of one or more symptoms presented by a patient suffering from a skin condition.

The term "topically acceptable carrier" is used herein to refer to a carrier considered by those skilled in the pharmaceutical, food or cosmetic arts to be non-toxic when used topically on human or other animal skin.

For some skin conditions, alleviating or treating the symptoms such as inflammation or erythema will result in treatment of the skin condition. For example, acne, eczema, wrinkling, sunburn, heat burn, keratosis and wound repair may be treated by the methods of the present invention.

For other skin conditions, alleviating or treating the symptoms may only partially alleviate the skin condition because the underlying causative medical condition is not addressed by the method. For example, treating the inflammation resulting from an allergy reaction will not address the influence of histamines causing the reaction. Other such skin conditions include psoriasis, acrodermatitis enteropathica, epidermolysis, gingivitis, lichenification, necrobiosis, dermatitis, scleroderma, ecthyma, ichthyosis, keloids and keratodermia. Full treatment or cure of these skin conditions may require use of additional treatments, for example, antihistamines, to target the driving force of allergic reactions.

A typical topical formulation for use in the method of the invention comprises:
(a) 0.1 to 10% by weight of the total composition of lauryliminodipropionic acid tocopheryl phosphate;
(b) 0.1 to 10% by weight of the total composition of glycerin;
(c) 0.01 to 5% by weight of the total composition of trisodium EDTA;
(d) 0.01 to 5% by weight of the total composition of carbomer (Carbopol Ultrez 10);
(e) 0.1 to 10% by weight of the total composition of cetearyl alcohol (and) Ceteareth-20 (Phoenoxol T);
(f) 0.1 to 5% by weight of the total composition of glyceryl stearate;
(g) 0.1 to 10% by weight of the total composition of isopropyl myristate;
(h) 0.1 to 10% by weight of the total composition of cetyl ethylhexanoate;
(i) 0.1 to 10% by weight of the total composition of isocetyl behenate;
(j) 0.1 to 10% by weight of the total composition of oleyl erucate;
(k) 0.01 to 5% by weight of the total composition of dimethicone;
(l) 0.01 to 5% by weight of the total composition of triethanolamine;
(m) 0.1 to 10% by weight of the total composition of propylene glycol, diazolidinyl urea, methylparaben, and propylparaben (Germaben II); and
(n) balance of the total composition of water.

The topical formulations used in the method of the invention may further comprise other active ingredients. Other active ingredients include but are not limited to antibiotics, antihistamines, antiseptics, disinfectants, antiinflammatories, keratolytic agents, steroids, antiandrogens, retinoids, salicylic acid, zinc oxide and sunscreens. One example of a suitable disinfectant is tea tree oil.

In a third aspect of the invention, there is provided a pharmaceutical kit for the topical treatment of erythema and inflammation associated with a skin condition, the kit comprising a first set of components and a second set of components, wherein said first set of components is selected from the group consisting of antibiotics, antihistamines, disinfectants, antiseptics, salicylic acid, a vitamin A derivative, antiinflammatories, keratolytic agents, sunscreens, and mixtures thereof; and said second set of components comprises one or more complexes of one or more phosphate derivatives of one or more electron transfer agents, wherein said first and second sets of components when mixed together form a composition for the topical treatment of a skin condition.

The term "antibiotic" is used herein to refer to chemical compounds having "antimicrobial" activity including bactericidal and/or bacteria static properties against microbes normally found in the skin of a patient suffering from acne, for example *Propionibacterium* acnes. Exemplary antibiotics include erythromycin, antibiotics of the lincomycin family, cephalosporins such as cephalexin, 7-(d-a-amino-a-phenylacetamido)-3-methyl-3-cephem-4-carboxylic acid monohydrate, and the tetracyclines.

The term "antibiotic of the lincomycin family" is used herein to refer to a class of antibiotic substances originally recovered from *streptomyces lincolnensis*. Exemplary antibiotics include lincomycin and clindamycin and their pharmaceutically acceptable salts and esters such as their hydrochlorides and phosphates. Lincomycin is a derivative of the amino acid trans-L-4-.alpha.-propyl-hygrinic acid coupled to a derivative of an octose substituted by a methylmercaptyl group. Clindamycin is the 7-deoxy, 7-chloro derivative of lincomycin, and is otherwise known as methyl 7-chloro-6,7,8,trideoxy-6-[[(1-methyl-4-propyl-2-pyrrolidinyl)carbonyl]amino]-1-thio-L-threo-.alpha.-D-galacto-octopyranoside.

The term "antibiotic of the tetracycline family" is used herein to refer to a class of antibiotic substances originally recovered from *streptomyces aureofaciens*. Exemplary tetracyclines include chlortetracycline, oxytetracycline, tetracycline, demeclocycline, rolitetracycline, methacycline and doxycycline and their pharmaceutically acceptable salts such as acid addition salts, for example, their hydrochloride salts. Tetracycline is otherwise known as 4-(Dimethylamino)-1,4,4a,5,5a,6,11,12a-octahydro-3,6,12,12a-pentahydroxy-6-methyl-1,-11dioxo-2-naphthacene-carboxamide.

In a fourth aspect of the invention, there is provided use of an effective skin-penetrating amount of one or more complexes of one or more phosphate derivatives of one or more electron transfer agents for preventing, alleviating symptoms or treating a skin condition of a subject.

In a fifth aspect of the invention, there is provided use of an effective skin-penetrating amount of one or more complexes of one or more phosphate derivatives of one or more electron transfer agents in the manufacture of a medicament for preventing, alleviating symptoms or treating a skin condition of a subject.

An advantage of the present invention relates to the surprising speedy onset of effectiveness and reproducibility of clinical benefit.

DETAILED DESCRIPTION OF THE INVENTION

The invention provides a general and benign treatment for preventing, alleviating symptoms or treating a skin condition. The treatment has been used for a wide variety of skin conditions that show an inflammatory or erythema response, and it has been successful where the causative agent has been removed. Excellent results have also been shown where the treatment is used before trauma or as prophylaxis to avoid erythema or inflammation. The treatment is unusual that it is emollient which can also limit pain and scarring. It is also noted that the epidermis is not thickened as is found after normal repair takes place.

The topical application of phosphate derivatives of electron transfer agents to a subject suffering from acne according to the present invention results in the rapid transport of electron transfer agent phosphate complexes through the stratum corneum and into the epidermis and dermis, with the consequences of reducing erythema (redness) due to acne, reduction of comedones, particularly reduction in the elevation of and inflammation of acne lesions, transformation of acne papules into macules (pink flat slightly raised acne lesions associated with terminal stages of acne), and thinning and softening of the epidermis. The method and composition according to the present invention can also be used prophylactically to assist in the regulation of epidermal biology, that is keratinization, thus preventing the appearance of acne comedones.

For the treatment or prevention of acne, the method of the invention would typically involve the daily use of a formulation according to the invention containing an amount in the range of 1 to 3% of one or more phosphate derivatives of one or more electron transfer agents. Preferably, the formulation would contain 1 to 3% of one or more complexes of one or more phosphate derivatives of one or more electron transfer agents. It is recommended that the formulation as a cream is liberally applied after cleansing to the areas that are susceptible to comedones, paying particular attention to areas that show some erythema. It has been found that gentle rubbing until the cream has been absorbed into the outer layers of the skin increases efficacy by ensuring that cream is not accidentally removed by the wiping action of clothes etc. Similarly, if a gel composition is used, wait for the gel to dry to avoid accidental removal. Where there is reason for suspecting an infection of the comedone, it is recommended that an antibiotic or disinfectant be applied prior to the use of the cream, as the phosphate derivatives of one or more electron transfer agents is not thought to have significant antibiotic activity. It has been found that tea tree oil is a suitable disinfectant.

For the treatment or prevention of rosacea, the method would typically involve the daily use of a formulation according to the invention containing an amount in the range of 1 to 3% of one or more phosphate derivatives of one or more electron transfer agents. Preferably, the formulation would contain 1 to 3% of one or more complexes of one or more phosphate derivatives of one or more electron transfer agents.

The topical application of phosphate derivatives of electron transfer agents to a subject suffering from scalding or excess exposure to the sun or chemical irritants, such as urea or urea products, if applied soon after the exposure results in the rapid transport of electron transfer agent phosphate complexes through the epidermis and into dermis, with the consequences of reducing erythema and pain, thinning and softening of the epidermis after only two to three days of use, and subsequently the reduction in the depth of wrinkles.

It is recommended that a formulation comprising 3% of one or more complexes of one or more phosphate derivatives of one or more electron transfer agents be used when there is reason to believe there is extensive damage such as sunburn or a formulation comprising 1% of one or more complexes of one or more phosphate derivatives of one or more electron transfer agents when prophylaxis is needed. The cream should be applied with gentle rubbing until effectively absorbed into the dermal layer. It should be noted that the erythema should be significantly attenuated within three minutes otherwise it is suggested that further cream be applied until the erythema is visibly attenuated.

For prophylactic use (eg protection from sunburn) it is recommended that formulation comprising 3% of one or more complexes of one or more phosphate derivatives of one or more electron transfer agents be applied at least 30 minutes prior to sun exposure. The cream should be applied liberally and to those areas of UV exposure. As an effective after sun care treatment, formulation comprising 1 to 3% of one or more complexes of one or more phosphate derivatives of one or more electron transfer agents should again be applied liberally over the affected areas for at least 3 days or until symptoms of inflammation such as pain and erythema have been suitably reduced.

For treatment of insect bites and stings, it is suggested that a liberal amount of a formulation comprising 3% or more of one or more complexes of one or more phosphate derivatives of one or more electron transfer agents be applied as soon as possible after sustaining the injury.

For treatment of dermatitis, it is suggested that formulation comprising 3% or more of one or more complexes of one or more phosphate derivatives of one or more electron transfer agents be applied upon presentation of typical inflammatory symptoms. The cream should be applied liberally to the affected area(s) and rubbed adequately into the skin to promote absorption. As an effective adjunct to treatment, formulation comprising 1 to 3% of one or more complexes of one or more phosphate derivatives of one or more electron transfer agents should be used to treat the affected areas until symptoms have been suitably reduced.

The phosphate derivatives of one or more electron transfer agents can be used alone or in combination with chemical and physical sunscreens to produce compositions, which exhibit enhanced overall protection from most forms of currently known oxidative tissue stressors. The compositions of the invention can be used as either or both pre and post-treatment to skin exposed to oxidative stress from any of the aforementioned stress factors. Furthermore, the phosphate derivatives of one or more electron transfer agents may include ascorbyl phosphates (that is, Vitamin C) to further promote healthy skin.

We have found that the increased penetration of tocopheryl phosphate complexes or other suitable phosphate complexes results in reduction of erythema and is likely to reduce epidermal thickening. Without wishing to be bound by theory, we believe that the reduction in erythema relates to the function of prostaglandins in the skin and the mechanism by which new skin is generated following trauma. This involves a variety of biochemical processes as well as the general immune system to rapidly replace the damaged cells and restore integrity. Although regulation of skin thickness is not entirely clear, the process is known to rely on binding of T cell growth factors to their receptors. This initiates a series of poorly understood events that culminate in mitotic activity or cutaneous growth. Interestingly, the process involves phosphorylation of several different T cell membrane and cytoplasmic second messenger proteins. Biochemistry of this second messenger signaling system is thought to rely on a phosphatase regulating T cell activation events. Tocopheryl phosphate has been shown to regulate phosphorylation of the membrane messenger or signal proteins. The same phosphatase then converts excess free tocopherol to tocopheryl phosphate preventing pro-oxidation. This auto regulatory feedback mechanism causes a steeper oxygen gradient and thinner epidermis.

Vitamins A, C, E, ubiquinol and bioactive compounds interact in a cascade to progressively reduce the chemical energy of the resultant free radicals and eventually annihilate them with counter free radicals. We also believe that tocopheryl phosphate supplementation stimulates activity of, regenerates and/or mobilizes transfer of retinyl phosphate producing all the benefits of vitamin A in the skin such as reduced keratinization of the pilosebaceous follicle and inflammation occurring with acne. Like vitamin E, vitamin A membrane absorption appears to be an active process. Dietary retinoids are transported across the intestinal membrane as retinyl phosphate, which has higher affinity for a membrane transfer protein (phosphatase). Topically delivered retinoids would also be better absorbed and quicker acting if delivered as the complexes of retinyl phosphate derivatives in accordance with the present invention.

We believe that tocopherol is one of the important guardians of the aforesaid phosphatase reaction. We therefore believe that increased availability of tocopherol, in the skin due to the formulation of the invention enhances the healing process or regulates normal homeostasis. The clinical benefit observed as a result of the higher skin penetration of tocopherol by the practice of the present invention is manifest as rapid reduction in erythema, amelioration of swelling and regulation of keratinosis that improve skin appearance, reduce epidermal thickness or crustiness and increase skin softness.

Electron transfer agents are physiologically important in the interfacial region where the dermis crosses over to epidermis, we have found that elevating the concentration of such agents leads to thinning and plasticising of the epidermis. This greater plasticity of the epidermis leads to an alleviation of the hardening of the skin from photo-aging and importantly removal of wrinkles.

A person skilled in the art will know what components may be used as the topically acceptable carrier for the compositions of the present invention. These will include excipients such as solvents, surfactants, emollients, preservatives, colorants, fragrances and the like.

The topical formulation used in the present invention may include additional surface-active agent or dispersing agent to disperse uniformly the active ingredients. A preferred composition includes a second surface-active agent. Such agents include the esters of polyols and sugars, the products of the condensation of ethylene oxide with fatty acids, fatty alcohols, long-chain alkylphenols, long-chain mercaptans, long chain amides, polyethers of polyhydroxylated fatty alcohols and alkylpolyglycol ethers which are included in an amount of from about 2% to about 6% by weight.

The topical formulation may be in the form of various cosmetic products including antiperspirant sticks, deodorant sticks, sunscreens, facial cleansers, make-up removers, hair pomades, facial gels, oil in water moisturizers, lotions, conditioners, shampoos, conditioning shampoos, toothpaste, and foaming body washes.

A preferred composition for oily skin is in the form of an aqueous gel, and the most preferred composition is an aqueous alcoholic gel. The aqueous gel is preferred for use on oily skin typically associated with acne. However, liquid suspensions and emulsions, as well as creams, ointments and powders are acceptable.

The method of the invention may involve delivery of the topical formulation via any suitable pharmaceutical delivery system applied to the skin including patches, gels, depots, plasters, aerosols and sustained or delayed release systems designed to alter absorption kinetics.

The topical formulation used in the method may be applied either simultaneously with or shortly prior to or after the application of another active ingredient selected from the group consisting of antibiotics, antihistamines, antiseptics, antiinflammatories, keratolytic agents, sunscreens and mixtures thereof to the skin of a patient suffering from erythema or inflammation associated with a skin condition. The other active ingredient may be applied as part of the topical formulation used in the method of the invention or they may separately be applied to the skin. In the latter practice, the other active ingredient is applied first to the skin and immediately or shortly thereafter the electron transfer agent phosphate complexes is applied or, the order of application is reversed.

If the topical formulation used in the method of the invention includes an antibiotic, the antibiotic may be present in an amount of about 0.01 to about 5 weight percent of the total composition, and preferably from about 0.1 to about 3 weight percent. Preferred antibiotics include erythromycin, or an antibiotic from the lincomycin or tetracycline families, a preferred form of the composition comprising tocopheryl phosphate complex and erythromycin or clindamycin or tetracycline or a pharmaceutically acceptable salt or ester thereof.

The gelling agent used in a preferred composition used in the method of this invention may be selected both as to type and quantity to give products of various viscosities. A variety of gelling agents may be used for the present purposes. Preferred gelling agents are pure microcrystalline cellulose, colloidal magnesium silicate, hydroxypropyl methylcellulose and the so-called hydroxylated vinylic polymers, particularly; those disclosed in U.S. Pat. No. 2,798,053. Those hydroxylated vinylic polymers of special interest herein can be described generally as interpolymers prepared from a monomeric mixture comprising a mono-olefinic acrylic acid and about 0.1% to about 10% by weight of the other monomers in the monomeric mixture of polyether of an oligosaccharide having hydroxyl groups which are etherified with allyl groups, said oligosaccharide containing at least two allyl groups per oligosaccharide molecule. Commercially available interpolymers of this type are marketed under the trademark Carbopols®. These are described as being polymers of acrylic acid cross-linked with about 1% of a polyalkyl ether of sucrose having an average of about 5.8 alkyl groups for each sucrose molecule. These polymers have molecular weight in the order of magnitude of 1,000,000. Such polymers are available from the B.F. Goodrich Chemical Company and are sold under such trademarks as Carbopol®. 940 and Carbopol®. 941. Closely related copolymers, such as Carbopol®. 1342 are also acceptable.

The amount of gelling agent included in the present preferred gel composition can range from about 0.1 to about 15% by weight, and preferably from about 0.5 to about 3% by weight, based on the total weight of the composition.

One type of preparation may comprise a two-component system, wherein one component comprises the antibiotic in stable form and the other component comprises the electron transfer agent phosphate complexes component. Another type of preparation comprises a composition in which the two active ingredients are stabilized as described hereinabove and may coexist relatively unchanged at temperatures conventionally employed for the storage of clindamycin or tetracycline solutions. Conventional pharmaceutical processes may be used in making up these common forms of topical compositions.

EXAMPLES

The following examples are illustrative of the present invention. In addition, the formulations in the examples in our co-pending international patent application no PCT/AU01/01476 may be used in methods according to the invention.

Study Example 1

This clinical study illustrated the efficacy of the a tocopheryl phosphate complex formulation when used in the method of treating patients with acne according to the invention.

A tocopheryl phosphate amphoteric complex formulation (TPC2) was prepared as follows:

| | |
|---|---|
| lauryliminodipropionic acid tocopheryl phosphate (30%) | 10.00 |
| Carbomer ultrez 3% | 12.00 |
| Preservative DMDMH | 0.10 |
| Triethanolamine 99% | 0.25 |
| D&C red 33 (0.4)% | 0.02 |
| Distilled water | 77.63 |

The control formulation was the vehicle without laurylimi-nodipropionic acid tocopheryl phosphate.

Pharmaceutical formulations suitable for use in treating acne can include:
(a) 1 to 10% by weight of the total composition of lauryliminodipropionic acid tocopheryl phosphate;
(b) 0.1 to 10% by weight of the total composition of Carbomer ultrez 3%;
(c) 0.1 to 10% by weight of the total composition of triethanolamine;
(d) optional colouring agents and preservatives; and
(e) balance of the total composition of water.

Method

At screening (Visit 1), prospective human patients were examined for the presence of inflammatory papules on the face. Patients qualified for study participation by having at least four equivalent inflammatory papules on the face (two on each side of the face), and a score of 3-5 on the Modified Cook Acne grading scale (see below). Qualified patients completed a health and eligibility questionnaire and signed an informed consent agreement.

At baseline (Visit 2), patients had a minimum of four equivalent inflammatory papules evaluated (equivalency was based on color and elevation). Each of the patient's papules were graded for lesion erythema and lesion elevation using an analog scale where 0=none/flat and 10=severe/very elevated. Irritation (erythema and scaling) surrounding each lesion was evaluated using a five-point scale (see Clinical Grading Scales below), and the grader recorded whether or not the lesion had resolved to a macule. Patients completed a self-assessment questionnaire to rate their perception of product benefit, and received two test materials (a tocopheryl phosphate complex treatment and a vehicle control), one to use on the right side of the face and one to use on the left side of the face according to a predetermined randomization. Patients also received a bar of Dove® (manufactured by Lever Brothers, USA) soap for facial cleansing and a daily diary. Patients were shown how to use the products prior to leaving the clinic, and were instructed to dispense the products onto clean fingertips and apply to designated blemishes nightly. Patients returned to the clinic after one (Visit 3), two (Visit 4), and five days (Visit 5) of product use and participated in clinical grading procedures as described for baseline. At the final study visit, patients returned any unused products and completed daily diaries.

| Clinical Grading Scales |  |
|---|---|
| (a) Modified Cook Acne Grading Scale | |
| 0 | Facial skin need not be perfectly clear. A few scattered comedones or papules may be present, but these should be visible only on close examination. |
| 1 | Comedones and small papules are present and noticeable from a distance of 1-3 ft away. |
| 2 | About one fourth of facial area is involved, with small papules (about six to 12) and comedones. A few pustules or large prominent papules may be present. |
| 3 | Approximately 30% (26-49%) of facial area is involved with small papules (13 to 20) and small comedones. A few pustules or large prominent papules may be present. |
| 4 | About half of facial area is involved, with small papules and large or small comedones. A few pustules or large prominent papules are usually present. (If lesions are generally large, subject may have a grade 4 severity, although less than half of facial area is involved.) |
| 5 | More than half (51-74%) of facial area is involved with large and small papules and comedones. (Lesser facial area of involvement is permissible if inflammatory lesions are large.) A moderate number of pustules are usually present, some of which may be large. |
| 6 | About three fourths of facial area is involved, with papules and/or large open comedones. (Lesser facial area of involvement is permissible if inflammatory lesions are large.) Numerous pustules are usually present, some of which may be large. |
| 7 | Greater than 75% but less than 85% of facial area is involved, with the majority of lesions being papules and large open comedones. Pustules may be large and prominent. |
| 8 | Practically all of facial area is involved. Large prominent pustules are usually visible. Lesions are usually highly inflammatory. Other types of acne (such as conglobata, including sinus and cystic types) may be present |

| (b) Surrounding Skin Erythema (pop. not screened for this) | |
|---|---|
| 0 | None |
| 1 | Very Mild (Barely perceptible redness/edema) |
| 2 | Mild (Perceptible, but mild redness/edema) |
| 3 | Moderate (Obvious redness/edema) |
| 4 | Severe (Marked, uniform redness/edema) |

| (c) Surrounding Skin Scaling | |
| --- | --- |
| 0 | None dryness/scaling |
| 1 | Mild dryness (Fine powdery appearance, barely perceptible) |
| 2 | Mild/Moderate dryness (Definite powdery appearance with some lifting edges) |
| 3 | Moderate dryness (Lifting edges over most of the grading site, some large loosely attached flakes) |
| 4 | Severe dryness (Large, loosely attached flakes over most of the grading area, possible fissuring) |

| (d) Lesion Scoring (analog scale) | | |
| --- | --- | --- |
| Elevation | 0 = flat | 10 = very elevated |
| Erythema | 0 = none | 10 = severe |

Clinical grading parameters for each visit were compared to baseline using a Paired t-Test. Comparisons between the treatments were made using ANOVA with Fisher's LSD. Frequency tables displaying papule to macule transition were created for each test material across time. Self-assessment questionnaires were tabulated and compared between the treatments using ANOVA with Fisher's LSD. All statistical comparisons were performed at $p \leq 0.05$ significance level.

Results

At baseline, and after one, two, and five days of test material use, patients were evaluated for lesion elevation and erythema, and surrounding skin scaling and erythema. The following table presents the results of the clinical grading. Mean scores are presented for each parameter at each grading time-point.

| | Results Of Facial Examinations | | | | | | | |
| --- | --- | --- | --- | --- | --- | --- | --- | --- |
| | TPC2 | | | | Control | | | |
| | Baseline (Visit 2) | Day 2 (Visit 3) | Day 3 (Visit 4) | Day 6 (Visit 5) | Baseline (Visit 2) | Day 2 (Visit 3) | Day 3 (Visit 4) | Day 6 (Visit 5) |
| Surrounding erythema | 0.90 | 0.40† | 0.60† | 0.45† | 1.00 | 0.20† | 0.40† | 0.55† |
| Surrounding scaling | 0.00 | 0.00 | 0.00 | 0.00 | 0.00 | 0.00 | 0.00 | 0.00 |
| Lesion elevation | 4.05 | 3.56† | 2.80† | 0.94† | 4.08 | 3.88 | 3.24† | 2.36† |
| Lesion erythema | 3.93 | 3.55† | 2.84† | 1.08† | 4.14 | 3.89† | 3.15† | 2.31† |

†Statistically significant ($p \leq 0.05$) decrease compared to baseline

Papule to Macule Transition Frequency

This table presents the papule to macule transition frequency for each treatment. Papule to macule transition indicates the treatment responsiveness/acne resolution dynamics.

| | | Visit 2 (Baseline) | Visit 3 (Day 2) | Visit 4 (Day 3) | Visit 5 (Day 6) |
| --- | --- | --- | --- | --- | --- |
| TPC2 | Papules | 20 | 20 | 19 | 11 |
| | Macules | 0 | 0 | 1 | 9 |
| Control | Papules | 20 | 20 | 20 | 19 |
| | Macules | 0 | 0 | 0 | 1 |

Results of this study show that TPC2 is significantly better than the vehicle in reducing the elevation of inflammatory acne (papules and pustules). This significant difference in reduction of lesion elevation was observed at days 2 and 6 of the study. TPC2 also significantly outperformed the vehicle in reducing inflammatory lesion redness by day 6 of the treatment period.

By day 6 of the treatment period, 9 out of 20 inflammatory lesions (45%) treated with TPC2 transformed into the macules, while only 1 out of 20 inflammatory lesions (5%) treated with the vehicle transformed into macules. Macules are considered the terminal stage of an inflammatory lesion before it resolves. TPC2 appears to help facilitate the transition of papules and pustules into macules. Results of the self-assessment questionnaires showed that by day 6, 90% of the subjects felt that TPC2 outperformed the Control in improving the appearance of papules and pustules.

Results of the study support the effectiveness of the present invention. Repetitive topical applications of a composition containing TPC2 are an effective therapy for reducing the elevation, redness and infection of inflammatory acne lesions in the acute stage of development. Current topical acne therapies improve inflammatory acne lesions either by promoting bactericidal activity (e.g. benzoyl peroxide) or keryolytic activity (e.g. salicylic acid or retinoids). The tocopherol phosphate amphoteric complex according to the invention does not have anti-microbial activity, in the traditional sense. The composition has surface activity and substantivity to keratin fibre that may slow down the keratinization process on the follicular cell walls and prevent or inhibit coalescence of the keratin through a peptizing effect at the liquid-solid interface (seburn-follicular cell wall). In addition, the formulation may inhibit or regulate the production of seburn and inhibit the generation of free radicals and or fatty acid levels, which indirectly leads to a lack of nutrient for microorganisms. It is also possible that high penetration of the tocopheryl phosphate amphoteric complex into the skin elicits a positive immune response, which restores the homeostasis within the skin and mitigates the pathology producing papules.

The method according to the invention is effective in reducing the size of the lesions from the papule stage to the macule stage, which is the final stage of acne.

Based on these results, similar results may be expected for other complexes of phosphate derivatives of electron transfer agents such as lauryliminodipropionic acid ubiquinyl phosphates; ubiquinyl phosphate arginine complexes; retinyl phosphate histadine complexes; oleyliminodipentanoic acid ascorbyl phosphates; linoleyliminidibutanoic acid tocotrienol phosphates; and palmyliminodiproprionic acid P:tocopheryl P:ascorbyl phosphate diesters.

Study Example 2

This study was conducted to determine the efficacy of tocopheryl phosphate complexes in improving clinical signs of erythema on patients as compared to tocopheryl acetate, a placebo, and reference controls.

Method

Five female human patients completed the study. Table 1 presents each patient's ethnicity, date of birth, and Fitzpatrick skin classification*. Ethnicity information was obtained from each patient's health and eligibility questionnaire.

TABLE 1

Patient Information

| Subject Number | Ethnicity | Date of Birth | Fitzpatrick Classification |
|---|---|---|---|
| 002 | Caucasian | May 19, 1968 | II |
| 003 | Caucasian | Dec. 21, 1958 | II |
| 004 | Caucasian | May 03, 1978 | II |
| 006 | Vietnamese | Apr. 20, 1963 | II |
| 007 | Caucasian | Jan. 24, 1965 | II |

* The Fitzpatrick skin classification is based on the skin's unprotected response to the first 30 to 45 minutes of sun exposure after a winter season without sun exposure:
I Always burns easily; never tans
II Always burns easily; tans minimally
III Burns moderately; tans gradually MED Determination (Day 1 and Day 2)

At Visit 1, prospective patients were examined on the back for the presence of scars, birthmarks, moles, vitiligo, keloids, skin abnormalities, tanning, erythema, or any other dermal markings. Patients who did not exhibit a skin condition that would interfere with the study qualified for study participation. Patients completed a health and eligibility questionnaire, and signed an informed consent agreement and a photography release form.

Each patient's inherent or unprotected MED (minimal erythema dose) was determined on the lower back. To determine the MED, each patient received approximately seven irradiation exposures on seven adjacent unprotected skin sites on the lower back. Each exposure represented a 25% increase in energy over the previous exposure. The sites were examined by a clinical grader for immediate erythema and immediate pigment darkening after the completion of each exposure.

UV radiation was supplied by an artificial source, which has a spectral output in the ultraviolet range comparable to that of the natural solar spectrum. A single port solar simulator with a 150-watt xenon arc lamp (Model 16S, Solar UV Simulator, Solar Light Co., Philadelphia) was used for irradiation. UVA and UVB radiation was obtained by using a combination of the UG-5 or UG-11 and WG-320 filters (Schott Glass Technologies) placed in the radiation path of the solar simulator. At a distance of 3 inches from the lamp housing (the distance at which radiation will strike the skin), the lamp emitted a 1 cm diameter "spot" of radiation. The radiation of the xenon bulb was measured using the 3D-600 meter (Solar light Co.) and measurements were taken at least 30 minutes after lamp warm-up. UVA/UVB radiation output was recorded in MED/hr/cm2 prior to MED determination and each day of irradiation.

At Visit 2, approximately 22 to 24 hours after completion of irradiation at Visit 1, the irradiated sites were examined for erythema using the following scale:

| | |
|---|---|
| − | No visible erythema |
| ? | Questionable response; unclear |
| + | Erythema, extending to the borders (MED) |
| ++ | Erythema, with or without edema present |

The site receiving the lowest dose of UV, which produced the first perceptible redness reaction with clearly defined borders (+), was selected as the MED for the patient.

Then during the pre-treatment and post-treatment phase, the patients were occlusively patched with a set of the following test materials on opposite sides of the lower back:

| | |
|---|---|
| 90/1 (3% lauryliminodipropionic acid tocopheryl phosphate) | Composition prepared as per example 3 below. |
| 90/2 (1% lauryliminodipropionic acid tocopheryl phosphate) | Composition of example 3 diluted to 1% active with water |
| 90/3 (0.5% lauryliminodipropionic acid tocopheryl phosphate) | Composition of example 3 diluted to 0.5% active with water |
| 90/4 (3% tocopheryl acetate) | Composition of example 3 with the lauryliminodipropionic acid tocopheryl phosphate replaced with tocopheryl acetate |
| 90/5 (Placebo) | Composition of example 3 without the lauryliminodipropionic acid tocopheryl phosphate |
| Steroid cream 0.1% - reference control | Commercial anti-inflammatory product where one gram of cream contains 1 mg mometasone furoate in an cream base of hexylene glycol, phosphoric acid, propylene glycol stearate, steryl alcohol and ceteareth-20, titanium dioxide, aluminium starch octenylsuccinate, white wax, white petrolatum and purified water. |
| Banana Boat ™ Aloe Vera Gel - reference control | Commercial product of Sun Pharmaceuticals, USA. |
| Undosed patch - untreated control | |

Pre-Treatment Evaluation Phase (Day 2 Through Day 10)

Patches were applied (to one side of the back) for three consecutive days (Day 2, Day 3, and Day 4), with the exception of the patch containing Banana Boat™ Aloe Vera Gel which was patched on Day 3, Day 4, and Day 5. All patches were worn for approximately 24 hours and removed by clinic staff. On Day 6, patches were removed by clinic staff and sites were wiped with dry gauze. The test and untreated sites received 1.0 MED of UVA/UVB light.

On Day 7 (approximately 24 hours post UV exposure) and on Day 8, Day 9, and Day 10, each test site was clinically graded for erythema and Minolta Chromameter (a*) measurements were taken to assess skin color. Results of the erythema grading were recorded using an analog scale, where 0=no redness and 10=bright redness. Minolta Chromameter a* measurements were taken to measure the red/green color component of the skin. Increases in the a* value were indicative of increasing erythema or red tone due to vascularization. Subjects' backs were photographed on Day 7, Day 8, and Day 10.

Post-Treatment Evaluation Phase (Day 3 Through Day 7)

On Day 3, patients received 2.0 MED of UVA/UVB light on one side of the back opposite of pre-treatment side). Immediately after UVA/UVB exposure, subjects were occlusively patched with the treatments on the post-treatment side of the lower back. The patches were applied for three consecutive days (Day 3, Day 4, and Day 5). Patches were worn for approximately 24 hours and removed by clinic staff. Clinical grading of erythema and Chromameter a* measurements were performed at each test site on Day 4, Day 5, Day 6, and Day 7. Patients' backs were photographed on Day 4, Day 5, and Day 7.

Results

Minolta Chromameter measurements (a*) were taken to assess skin color (erythema) and clinical grading of erythema was performed for each test site on the indicated days:

Pre-treatment: Day 7, Day 8, Day 9, and Day 10
Post-treatment: Day 4, Day 5, Day 6, and Day 7

The following tables present the results of the erythema grading and Chromameter measurements. Mean scores are presented for each test material at each time point. A decrease in mean values indicates an improvement/reduction in erythema and redness.

| | PRE-TREATMENT EVALUATION | | | | | | | |
|---|---|---|---|---|---|---|---|---|
| | Clinical Grading of Erythema | | | | Chromameter (a*) | | | |
| | Day 7 | Day 8 | Day 9 | Day 10 | Day 7 | Day 8 | Day 9 | Day 10 |
| 90/1 | 1.10 | 0.80 | 0.30 | 0.30 | 9.13 | 9.40 | 7.66 | 8.35 |
| 90/2 | 1.10 | 0.80 | 0.40 | 0.40 | 11.69 | 8.69 | 8.17 | 8.42 |
| 90/3 | 1.30 | 0.90 | 0.60 | 0.50 | 12.04 | 10.11 | 9.87 | 9.47 |
| Banana Boat Aloe Vera Gel | 1.60 | 1.20 | 0.70 | 0.70 | 12.31 | 9.02 | 9.04 | 8.45 |
| 90/4 | 1.50 | 1.10 | 0.70 | 0.70 | 11.81 | 10.42 | 9.08 | 9.82 |
| 90/5 | 1.60 | 1.20 | 0.90 | 0.90 | 13.57 | 11.32 | 9.66 | 10.52 |
| Steroid cream | 1.10 | 0.80 | 0.60 | 0.50 | 11.87 | 10.45 | 10.19 | 9.53 |
| Undosed patch | 1.60 | 1.20 | 0.90 | 0.80 | 11.64 | 10.32 | 9.64 | 9.61 |

| | POST-TREATMENT EVALUATION | | | | | | | |
|---|---|---|---|---|---|---|---|---|
| | Clinical Grading of Erythema | | | | Chromameter (a*) | | | |
| | Day 4 | Day 5 | Day 6 | Day 7 | Day 4 | Day 5 | Day 6 | Day 7 |
| 90/1 | 2.60 | 1.70 | 1.20 | 1.10 | 12.23 | 10.98 | 11.45 | 10.54 |
| 90/2 | 2.60 | 1.70 | 1.40 | 1.20 | 14.94 | 13.36 | 9.20 | 8.92 |
| 90/3 | 2.60 | 1.90 | 1.70 | 1.50 | 13.67 | 11.62 | 10.64 | 10.75 |
| Banana Boat Aloe Vera Gel | 2.80 | 2.50 | 2.63 | 1.80 | 13.54 | 12.00 | 12.59 | 12.60 |
| 90/4 | 2.60 | 2.70 | 2.50 | 1.80 | 15.09 | 13.12 | 12.07 | 10.30 |
| 90/5 | 2.80 | 2.80 | 2.50 | 1.80 | 14.99 | 12.11 | 11.03 | 9.68 |
| Steroid cream | 1.40 | 1.10 | 0.80 | 0.80 | 9.45 | 6.67 | 7.57 | 8.55 |
| Undosed patch | 2.60 | 2.50 | 2.25 | 1.75 | 14.84 | 10.76 | 8.20 | 9.22 |

Discussion

Pre-Treatment

Treatment of back skin with 3% lauryliminodipropionic acid tocopheryl phosphate (tocopheryl phosphate complex), 1% lauryliminodipropionic acid tocopheryl phosphate (tocopheryl phosphate complex), 0.5% lauryliminodipropionic acid tocopheryl phosphate (tocopheryl phosphate complex) and steroid cream for three consecutive days prior to exposure to 1.0 MED of UV light resulted in lower erythema scores compared to sites treated with Banana Boat™ Aloe Vera Gel, the Placebo, 3% tocopheryl acetate, and the untreated control exposed to UV light. Differences in degrees of redness between the test materials were noticeable as early as Day 7 (24 hours post UV exposure) through Day 10. The 3% lauryliminodipropionic acid tocopheryl phosphate and 1% lauryliminodipropionic acid tocopheryl phosphate outperformed 0.5% lauryliminodipropionic acid tocopheryl phosphate and steroid in reducing erythema on Day 9 (72 hours post UV exposure).

Test sites treated with 3% lauryliminodipropionic acid tocopheryl phosphate and 1% lauryliminodipropionic acid tocopheryl phosphate had lower average Chromameter a* readings on Day 9 compared to sites treated with Aloe Vera Gel, the Placebo, 3% tocopheryl acetate, 0.5% lauryliminodipropionic acid tocopheryl phosphate, the steroid cream as well as the untreated site.

Post-Treatment

Treatment of back skin with 3% lauryliminodipropionic acid tocopheryl phosphate, 1% lauryliminodipropionic acid tocopheryl phosphate, 0.5% lauryliminodipropionic acid tocopheryl phosphate and steriod cream for 3 consecutive days following exposure to 2.0 MED of UV light resulted in lower erythema scores compared to sites treated with Aloe Vera Gel, the Placebo, 3% tocopheryl acetate, and the untreated control. Differences in degrees of redness between the test materials were noticeable as early as Day 4. The steroid cream outperformed all test samples in reducing erythema. The 3% lauryliminodipropionic acid tocopheryl phosphate and 1% lauryliminodipropionic acid tocopheryl phosphate outperformed 0.5% lauryliminodipropionic acid tocopheryl phosphate in reducing erythema on Day 4-7. Test sites treated with the steroid cream and 1% tocopheryl phosphate complexes had lower average Chromameter a* readings on Days 4 and 7 compared to treatment sites and the untreated control site.

Conclusion

This example demonstrates that complexes of phosphate derivatives of electron transfer agents such as lauryliminodipropionic acid tocopheryl phosphate are able to prevent and treat ultra-violet light induced erythema.

Based on these results, similar results may be expected for other complexes of phosphate derivatives of electron transfer agents such as lauryliminodipropionic acid ubiquinyl phosphates; ubiquinyl phosphate arginine complexes; retinyl phosphate histadine complexes; oleyliminodipentanoic acid ascorbyl phosphates; linoleyliminidibutanoic acid tocotrienol phosphates; and palmyliminodiproprionic acid P:tocopheryl P:ascorbyl phosphate diesters.

Example 3

A pre and post skin anti-erythema product for use in the method of treatment or prevention of erythema or inflammation associated with sunburn according to the invention was prepared as follows.

|   | INGREDIENTS | % WW | SUPPLIER |
|---|---|---|---|
| A) | Lauryliminodipropionic Acid Tocopheryl Phosphate - 30% | 10.00 | Vital Personal Care Specialties, Inc. |
|   | Ultrez Carbopol - 3% | 12.00 | B. F. Goodrich |
|   | Water Distilled | q.s. 100% |   |
| B) | triethanolamine - 99% | 0.25 | Union Carbide |
|   | Water Distilled preservative & dyes | 40.13 |   |

Example 4

A cream for use in the methods according to the invention was prepared as follows:

|   | W/W |
|---|---|
| PHASE A |   |
| Deionized water | 61.95% |
| Glycerin | 5.00 |
| Trisodium EDTA | 0.05 |
| Carbomer (Carbopol Ultrez 10)[2] | 0.50 |
| Lauryliminodipropionic Acid Tocopheryl Phosphate[1] | 7.50 |
| PHASE B |   |
| Cetearyl Alcohol (and) Ceteareth-20 (Phoenoxol T)[3] | 2.00 |
| Glyceryl Stearate (Emerest 2400)[4] | 1.00 |
| Isopropyl Myristate (Pelemol IPM)[3] | 5.00 |
| Cetyl Ethylhexanoate (Pelemol 168)[3] | 3.50 |
| Isocetyl Behenate (Pelemol ICB)[3] | 3.50 |
| Oleyl Erucate (Cetiol J-600)[4] | 3.00 |
| Dimethicone (Dow 200,100 cSt.)[5] | 0.50 |
| PHASE C |   |
| Deionized Water | 5.00 |
| Triethanolamine (99%) | 0.50 |
| PHASE D |   |
| Propylene Glycol (and) Diazolidinyl Urea (and) Methylparaben (and) Propylparaben (Germaben II)[6] | 1.00 |
|   | 100.00% |

Procedure:

Procedure: Combine Phase A items minus the Carbomer and Lauryliminodipropionic Acid Tocopheryl Phosphate. When a solution is obtained, disperse Carbomer in this solution. Begin heating Phase A to 70-75° C. with adequate agitation. Disperse Lauryliminodipropionic Acid Tocopheryl Phosphate in Carbomer mucilage with sweep agitation. Combine Phase B items and heat to 75-80° C. with adequate agitation. With Phase A uniform and at 70-75° C. and Phase B uniform and at 75-80° C. Add Phase B to Phase A with adequate agitation. Allow AB to cool to 50° C. and then add Phase C solution to AB. Continue adequate agitation of ABC until 45° C. is reached. Add Phase D to ABC. Continue adequate agitation until 35° C. is reached.

| 1. | Vital PC, Incorporated |
| 2. | B. F. Goodrich, Incorporated |
| 3. | Phoenix Chemical, Incorporated |
| 4. | Cognis, Incorporated |
| 5. | Dow-Corning, Incorporated |
| 6. | ISP Corporation |

Study Example 5

An eight-week double blind vehicle controlled pilot study was conducted to evaluate the effects of a topical treatment comprising tocopheryl phosphate complexes on improving the appearance of photodamaged skin. Ten female subjects completed the pilot study.

Procedures and Methods

At Visit 1 (screening), prospective subjects completed a health and eligibility questionnaire, and signed a photography release form and an informed consent agreement. Subjects were examined for study eligibility criteria according to the following classifications:

Fitzpatrick Skin Classification (Types I-IV Qualify)

Based on unprotected skin's response to the first 30-45 minutes of sun exposure after a winter season without sun exposure:

I Always burns easily; never tans
II Always burns easily; tans minimally
III Burns moderately; tans gradually
IV Burns minimally; always tans well
V Rarely burns; tans profusely
VI Never burns; deeply pigmented Modified Glogau Classification [Facial Photodamage] (Classifications I-II Qualify)

I Mild: no keratoses or scarring; little wrinkling
II Moderate: early actinic keratoses—slight yellow skin; discoloration; early wrinkling—parallel smile line
III Advanced: actinic keratoses—obvious yellow skin; discoloration with telangiectasia; wrinkling—present at rest
IV Severe: actinic keratoses; skin cancers have occurred; wrinkling—much cutis laxa of actinic, gravitational, and dynamic origin Subjects who qualified according to study eligibility criteria participated in a 3 to 7 day washout period. During this time moisturizing products were not used on the face.

Qualified subjects returned to the clinic for Visit 2 (baseline). Subjects participated in the following clinical grading and instrumentation procedures:

Objective irritation (erythema, edema, scaling/skin dryness, rash) and subjective irritation (burning, itching, stinging, tingling, tightness) were assessed globally on the face. Results were recorded using the following scale: 0=none, 1=mild, 2=moderate, and 3=severe.

The following efficacy (aging) parameters were graded at the specified locations using a analog scale (extremes of the scale are listed in parentheses).

| Fine Lines - left periocular area | (0 = none, 10 = severe) |
| Wrinkles - left periocular area | (0 = none, 10 = severe) |
| Pore Size - cheeks | (0 = small, 10 = large) |
| Mottled Pigmentation - face | (0 = none, 10 = severe) |
| Overall Skin Appearance - face | (0 = healthy, 10 = unhealthy) |

Triplicate pinch recoil measurements were taken to measure skin elasticity. Timed measurements were recorded to the nearest hundredth of a second.

Silicone replicas were taken of the left periocular (crow's feet) area to assess texture changes in the skin.

Photographs were taken of the left side of each subject's face.

Subjects were assigned to use test material Product A (cream from Example 4) or Product B (Vehicle control: emulsion system) according to a predetermined randomization. The appropriate test material was distributed to subjects and they were instructed to apply the test material to the face each morning and evening after cleansing. Subjects assigned to use test Product A were also provided with a moisturizer to apply after each test material application. Subjects were provided with a daily diary to record test material application times and comments.

Subjects returned to the clinic after four weeks (Visit 3) and eight weeks (Visit 4) of test material usage. At each visit, all clinical grading, photography, and silicone replicas were performed as described for baseline. Subjects completed a self-assessment questionnaire. At the completion of Visit 4, subjects returned unused test material and completed diaries to the clinic.

Mean scores for clinical grading parameters and pinch recoil measurements at Week 4 and Week 8 were statistically compared to baseline using a paired t-test at the $p \leq 0.05$ significance level. Mean percent change from baseline was calculated for all attributes. Comparisons were made between the test product and vehicle control using ANOVA with paired comparisons (Fisher's LSD). For self-assessment questionnaire responses at Week 4 and Week 8, mean response values and standard deviations were calculated for each question.

Results

At baseline and after four and eight weeks of test material use, subjects participated in clinical grading of the face and pinch recoil measurements. Table 2 presents the results of the efficacy grading, including pinch recoil measurements, and irritation parameter grading. Mean scores are presented for each grading time-point.

Irritation parameters were graded according to a four-point scale where 0=None, 1=Mild, 2=Moderate, and 3=Severe. Efficacy parameters were assessed according to an analog scale where 0 represents positive scores and 10 represents negative scores.

TABLE 2

MEAN SCORES FOR CLINICAL GRADING AND PINCH RECOIL MEASUREMENTS

| | Product A (n = 7) | | | Product B (n = 3) | | |
|---|---|---|---|---|---|---|
| | Baseline | Week 4 | Week 8 | Baseline | Week 4 | Week 8 |
| IRRITATION | | | | | | |
| Erythema | 0.14 | 0.00 | 0.14 | 0.33 | 0.33 | 0.33 |
| Edema | 0.00 | 0.00 | 0.00 | 0.00 | 0.00 | 0.00 |
| Scaling | 0.00 | 0.00 | 0.00 | 0.00 | 0.67 | 0.00 |
| Burning | 0.00 | 0.00 | 0.00 | 0.00 | 0.00 | 0.00 |
| Stinging | 0.00 | 0.00 | 0.00 | 0.00 | 0.00 | 0.00 |
| Itching | 0.00 | 0.00 | 0.00 | 0.00 | 0.00 | 0.00 |
| Tightness | 0.14 | 0.00 | 0.00 | 0.00 | 0.33 | 0.00 |
| Tingling | 0.00 | 0.00 | 0.00 | 0.00 | 0.00 | 0.00 |
| Rash | 0.00 | 0.00 | 0.14 | 0.00 | 0.00 | 0.00 |
| EFFICACY | | | | | | |
| Fine Lines | 4.07 | 3.14 ⇓ | 2.43 ⇓ | 3.50 | 3.33 | 3.25 |
| Wrinkles | 3.39 | 2.96 ⇓ | 2.36 ⇓ | 3.67 | 3.58 | 3.25 |
| PoreSize | 6.18 | 5.57 | 4.68 ⇓ | 4.25 | 4.08 | 4.00 |
| Mottled Pigmentation | 3.82 | 3.57 | 3.14 | 3.50 | 3.50 | 3.58 |
| Overall Skin Appearance | 5.46 | 4.68 ⇓ | 3.68 ⇓ | 6.67 | 6.58 | 6.17 |
| Pinch Recoil (seconds) | 1.89 | 1.56 ⇓ | 1.46 ⇓ | 1.87 | 1.94 | 1.81 |

⇓Indicates a statistically significant ($p \leq 0.05$) decrease compared to baseline Statistical comparisons, based on average change compared to baseline, revealed the following significant differences between the test materials:

Product A showed a greater significant decrease (improvement) for overall skin appearance at Week 4 and Week 8 compared to Product B.

At Week 4 and Week 8, subjects completed self-assessment questionnaires. Response means for each question were calculated by assigning each response option a numerical value as follows: 1=Disagree Strongly; 2=Disagree Somewhat; 3=Neither Agree nor Disagree; 4=Agree Somewhat and 5=Agree Strongly.

Table 3 presents the results of the mean questionnaire response calculations. Please note that mean values higher than 3.0 indicate an average positive response.

TABLE 3

MEAN SCORES FOR QUESTIONNAIRE RESPONSES

| | Product A (n = 7) | | Product B (n = 3) | |
|---|---|---|---|---|
| | Week 4 | Week 8 | Week 4 | Week 8 |
| Product improved overall appearance of fine lines and wrinkles compared with beginning of study | 4.00 | 4.00 | 2.67 | 3.33 |

TABLE 3-continued

MEAN SCORES FOR QUESTIONNAIRE RESPONSES

|  | Product A (n = 7) | | Product B (n = 3) | |
| --- | --- | --- | --- | --- |
|  | Week 4 | Week 8 | Week 4 | Week 8 |
| Product improved uneven skin color compared with beginning of study | 4.00 | 3.71 | 3.00 | 3.33 |
| Product reduced size of my pores compared with beginning of study | 4.00 | 3.71 | 3.33 | 3.00 |

Statistical comparisons, based on mean scores, revealed no statistically significant differences between the two test materials for questionnaire responses.

Discussion and Conclusions

Results of the study showed that the test product (Product A) showed significant improvements in the appearance of fine lines, wrinkles, and healthy skin appearance at 4 weeks and 8 weeks. No significant changes were observed in mottled pigmentation. The test product improved the appearance of facial pores at the 8-week visit compared to baseline values. The vehicle control (Product B) did not show significant improvements in any of these parameters at either visit.

The pinch recoil test was used to assess changes in skin elasticity. Product A produced significant improvements in pinch recoil times compared to baseline values at both the 4-week and 8-week visits. Product B did not improve pinch recoil times compared to baseline at either visit. Neither of the products produced significant increases in objective or subjective irritation at either visit.

Although Product A produced clinical improvements in the appearance of fine lines and wrinkles, silicone replicas taken at baseline, Week 4 and Week 8 were not sensitive enough to detect these changes. This discrepancy can be explained by the fact that Product A softens the appearance of fine lines and wrinkles at the most distal edge. This can be detected in clinical observation using a ring light with magnifying lens. In contrast, replicas analysis programs are designed to detect changes that occur over the entire length of the fine line or wrinkle. The subtle improvements in fine lines and wrinkles produced by Product A could not be detected using the silicone replica method.

Additionally, half-face photographs taken at baseline, Week 4 and Week 8 did not capture the improvements in fine lines and wrinkles from using Product A. The focal length between the camera and subject was too great to capture subtle improvements occurring at the distal edge from using Product A.

The favorable outcome of this pilot study suggests that Lauryliminodipropionic Acid Tocopheryl Phosphate improved the appearance of fine lines, wrinkles and skin elasticity in photodamaged skin. Compared to baseline scores Lauryliminodipropionic Acid Tocopheryl Phosphate improved pore appearance in the test group. Further, Lauryliminodipropionic Acid Tocopheryl Phosphate did not produce objective or subjective skin irritation responses in users.

Based on these results, similar results may be expected for other complexes of phosphate derivatives of electron transfer agents such as lauryliminodipropionic acid ubiquinyl phosphates; ubiquinyl phosphate arginine complexes; retinyl phosphate histidine complexes; oleyliminodipentanoic acid ascorbyl phosphates; linoleyliminidibutanoic acid tocotrienol phosphates; and palmyliminodiproprionic acid P:tocopheryl P:ascorbyl phosphate diesters.

Example 6

In this example, the method of the invention is used to treat erythema and inflammation symptoms associated with a heat burn.

A subject brushed his underarm on a hot exhaust pipe which produced a painful red wheal approximately 100 mm by 40 mm. He applied the cream from Example 4 within 10 minutes, gently spreading it from the perimeter to the center. Surprisingly, the pain was alleviated within 30 seconds and a blister did not form. Within two days, the burn had healed so much that it was difficult to identify the burnt area with the naked eye.

Example 7

In this example, a method of the invention is used to treat erythema and inflammation symptoms associated with dermatitis.

A subject with dermatitis affecting the arm, neck and chest was treated with the cream from Example 4. Surprisingly, the itchiness, irritation and scaliness were significantly reduced within one day of application. The subject noticed a marked improvement especially where the condition had caused cracked epidermis. Within a week of daily use, the condition was completely treated, so that skin irritation and erythema over the entire area was no longer visible. The subject was delighted that after years of very intrusive irritation and cracking of the skin, the symptoms of her condition had surprisingly gone.

Example 8

In this example, the method of the invention is used to treat erythema and inflammation symptoms associated with sebhorratic dermatitis.

A subject with sebhorratic dermatitis, that had become progressively more extensive over 3 weeks, applied a generous amount of a mixture of 0.5 mL tea tree oil and 30 g of the cream from Example 4 to the affected scalp area with an applicator. The cream was rubbed gently with the applicator into the affected area without causing pain but adequately enough to promote adsorption. Overnight the itchiness, scaling and infection had been eliminated. Surprisingly, the other symptoms of inflammation including erythema had also been eliminated. Recurrent symptoms did not appear for several weeks. When the symptoms did appear, they once again quickly abated when treated overnight with the above mixture.

Example 9

In this example, a method of the invention is used to treat erythema and inflammation symptoms associated with an insect bite.

A subject suffered a bite that caused severe blistering and inflammation covering an area on the lower leg approximately 60 mm×50 mm. After treatment with oral anti-histamine (180 mg fexofenadine hydrochloride nocte) and topical corticosteroid cream (0.5% hydrocortisone acetate) little improvement was noticed. On the second day the subject substituted the topical cotisone cream for the cream from Example 4 and continued daily treatment. One day following application of the cream from Example 4, the subject noticed a reduction in the blistering. Importantly, itchiness (a sign of healing and improved blood flow) around the trauma significantly increased and within 3 days after initial application of the cream from Example 4, blistering and inflammation had abated. The blisters then dried and within another 7 days the injured skin had fallen off, leaving a faint discolouration of the skin pigment.

Example 10

In this example, a method of the invention is used to treat erythema and inflammation symptoms associated with a heat burn.

A subject suffered a burn 3 to 4 mm deep with a 12 mm diameter from molten plastic adhering to the skin. The wheal formed was 25 mm in diameter. The subject immersed the wrist in running cold water for 3 to 5 minutes, then after removing the water applied the cream from Example 4. Within 3 minutes, all sensation of pain was gone and within 6 hours the erythema had disappeared. The burn was kept moist with the cream from Example 4 covered with a bandage for 3 days. No blister formed over the wound area but a depression remained and a scab eventually formed. The cream was applied occasionally for the next two weeks and within 2 weeks the scab had disappeared and a scar remained. The scar was not keloid or even very noticeable and no epidermal thickening was present.

Example 11

In this example, a method of the invention is used to treat erythema and inflammation symptoms associated with rosacea.

A first subject had suffered persistent rosacea on the cheeks for at least 5 years. The cream of Example 4 was applied over a period of 2 weeks during the summer period where the symptoms are most severe and although the condition was still apparent a very marked improvement had occurred. A second subject with similar aetiology reported a total loss of visible symptoms following 6 weeks daily application of the cream from Example 4.

Example 12

In this example, the method of the invention is used to treat the symptoms of sunburn.

A subject exposed to extreme sun damage of the skin with marked sensitization to touch applied the cream from Example 4, fifteen minutes after the trauma and was surprised that the pain was relieved within a minute but was more surprised that the expected peeling of the epidermis that normally follows such trauma, did not occur.

Example 13

In this example, the method of the invention is used to treat a freckle.

A subject had a large freckle on the cheek and over a period of a month applied the cream from Example 4 locally to the freckle and after the treatment the perimeter of the freckle was just distinguishable from the background skin but the color had reduced to the point that it was no longer apparent to casual examination. This was a surprising result as the freckle in question had been present for more than twenty years.

Example 14

In this example a dark skinned subject had a sharp and bleeding laceration, approximately 30 mm long and applied the cream from Example 4 to the wound before pulling the edges of the wound together with a bandage. Surprisingly the next day the wound showed no typical redness and no longer required bandaging to hold the wound together, More surprisingly the typical scarring that follows an inflammatory response was not present and the pigmentation around such scar was not present.

The following pharmaceutical compositions were prepared and were suitable for use in the methods according to the invention. In the following examples, "VPCS" refers to Vital Personal Care Services.

Pharmaceutical Composition Example 15

A lotion for use in the method of treatment of erythema and inflammation associated with acne according to the invention was prepared as follows. The following ingredients were mixed.

| Ingredient | w/w percent |
| --- | --- |
| cetyl alcohol | 0.75 |
| C12-15 alcohols benzoate | 5 |
| butylated hydroxyanisole | 0.1 |
| PEG-100 stearate | 0.25 |
| water, deionized or distilled | 70.4 |
| propylene glycol | 3.0 |
| lauryliminodipropionic acid tocopheryl phosphate | 10.5 |
| acetone | 10.0 |

Optionally, the composition may also include an antibiotic, such as clindamycin hydrochloride in about a 1 percent w/w amount. A further option is to prepare a second container including a solution of clindamycin hydrochloride (1% w/w of the total weight of the total composition) in an appropriate solvent, preferably water or ethanol. The amount of solvent used comprises an amount, which dissolves about 2 grams of clindamycin HCl in about 3 cc of solvent. Both containers may be put in a single marketable package with the instructions that the contents of the two containers be thoroughly mixed prior to the composition's application to the skin.

For each 3 cc of solution in the second container, the first container contains about 20 grams of composition. An alternate method comprises the stepwise application of the composition in the first container and the clindamycin solution in the second container so that the two-part composition is mixed on the skin.

Pharmaceutical Composition Example 16

A cream for use in the method of treatment of erythema and inflammation associated with acne according to the invention was manufactured by mixing the following ingredients:

| Ingredients | W/w percent |
| --- | --- |
| cetyl-stearyl alcohol | 1.25 |
| C12-15 alcohol benzoate | 5 |
| butylated hydroxyanisole | 0.01 |
| PEG-100 stearate | 0.85 |
| water, deionized or distilled | 69.1 |
| propylene glycol | 3 |
| lauryliminodipropionic acid tocopheryl phosphate | 10.5 |
| acetone | 10 |

Optionally, the composition may also include a keratolytic agent, such as salicylic acid in about a 1 percent w/w amount.

Pharmaceutical Composition Example 17

A gel for use in the method of treatment of erythema and inflammation associated with acne according to the invention was prepared by combining the following ingredients.

| Ingredient | W/w percent |
|---|---|
| water, deionized or distilled | 50.65 |
| Veegum .RTM. (R. T. Vanderbilt Co.) | 1.5 |
| carboxy vinyl polymer (acid) | 1 |
| diisopropanolamine | 0.75 |
| ethyl alcohol, 200. degree. | 30.1 |
| lauryliminodipropionic acid tocopheryl phosphate | 15 |

Optionally, the tocopheryl phosphate complex gel composition may be also include an antibiotic, such as clindamycin hydrochloride in about a 2 percent w/w amount. A further option is to prepare clindamycin phosphate (3% w/w of the total gel weight) is included in a second container.

Pharmaceutical Composition Example 18

Lincomycin was substituted for clindamycin or the salicylic acid in the compositions of Examples 15 to 17.

Pharmaceutical Composition Example 19

Tetracycline was substituted for clindamycin or the salicylic acid in the compositions of Examples 15 to 17.

Pharmaceutical Composition Example 20

Fifteen mg of Carbomer (15 mg) was added to distilled water (495 mg) while stirring. Stirring continued for about 45 minutes. A solution of sodium hydroxide (4.09 mg) in distilled water (4.9 mL) was added and stirring continued for 10 minutes. Ethyl alcohol (150 mL) and methyl salicylate (1 mg) were added to the stirred solution, followed by lauryliminodipropionic acid tocopheryl phosphate (in a 50% water solution) (400 mg), and distilled water (80 mL). The resulting mixture was stirred until a smooth gel was obtained. A 20 g sample of the gel was mixed with a solution of clindamycin hydrochloride (800 mg) in distilled water (3 mL) affording a gel containing about 17 g of TPC and 34.4 mg of clindamycin hydrochloride per gram of gel. The gel was suitable for use in the method of treatment of erythema and inflammation associated with acne according to the invention.

Pharmaceutical Composition Example 21

The following gel formulation for use in the method of treatment of erythema and inflammation associated with acne according to the invention including tetracycline was prepared according to the procedure in Example 20.

| Ingredient | W/w percent |
|---|---|
| lauryliminodipropionic acid tocopheryl phosphate | 20 |
| tetracycline | 2 |
| ethyl alcohol | 20 |
| PEG-8 caprate | 6 |

-continued

| Ingredient | W/w percent |
|---|---|
| colloidal mg aluminum silicate | 2.5 |
| hydroxyethylmethylcellulose | 0.75 |
| citric acid | 0.05 |
| water | Q.S. |

The resultant product had good stability and was effective for use in the treatment of erythema and inflammation associated with acne.

Pharmaceutical Composition Example 22

Aqueous gel composition for use in the method of treatment of erythema and inflammation associated with acne according to the invention was prepared according to the following formulation:

| Ingredient | W/w percent |
|---|---|
| lauryliminodipropionic acid tocopheryl phosphate | 15 |
| retin A | 0.5 |
| Carbomer.RTM. 940 | 1 |
| sodium hydroxide to desired pH | QS |
| water | QS |

The composition of the present invention may be applied to the afflicted skin of an acne sufferer for a period of time on a regular basis such that the erythema and inflammation associated with acne is brought under control. A preferred regimen of treatment comprises the application of the composition from about one to about four times a day.

Cosmetic Composition Example 23

A lotion with sunscreen for use in the method of treatment or prevention of erythema and inflammation associated with sunburn according to the invention was prepared as follows.

| | Ingredients | % w/w | Supplier |
|---|---|---|---|
| A) | Brij 72 (POE 2 Stearyl Ether) | 0.5 | Unichema Americas |
| | Emerest 132 (Stearic Acid) | 2.0 | Cognis |
| | Pelemol PDD (Propylene Glycol Dicaprylate/Dicaprate) | 10.0 | Phoenix |
| | Drakeol 9 (LT Mineral Oil) | 9.0 | Penreco |
| | Brij 721 (POE 21 Stearyl Ether) | 1.0 | Uniqema Americas |
| | Octylmethoxy Cinnamate | 7.0 | |
| | Benzophenane-3 | 2.0 | |
| | Dicorning 200 Fluid (Dimethicane) | 1.0 | |
| | Propyl Paraben | 0.1 | |
| B) | Cabopol Ultrez 10 Slurry 3% | 5.0 | |
| | Water | 10.0 | |
| C) | TEA 99% | 1.2 | |
| | Water Distilled | 10.0 | |
| | Methyl Paraben | 0.25 | |
| | lauryliminodipropionic acid tocopheryl phosphate - 40% with DMDMH | 7.5 | |
| | Water Distilled q.s. | 33.45 | |

A and C were heated separately to 80° C. A was added to C while mixing with an homogenizer for 2 to 3 min. The mixture was removed from the homogenizer, and B (which has been heated to 70° C.) was added and then the product cooled to room temperature.

Cosmetic Composition Example 24

A toothpaste for use in the method of treatment or prevention of erythema and inflammation associated with gingivitis according to the invention was prepared as follows:

|   | Ingredients | % w/w | Supplier |
|---|---|---|---|
| A) | Sorbitol USP | 15.0 | |
|   | 40% lauryliminodipropionic acid tocopheryl phosphate | 7.5 | |
| B) | Glycerin USP 96% | 10.0 | |
|   | Triclosan | 0.3 | |
|   | Na-Saccharin USP 40/60 Mesh | 0.2 | |
|   | Veegum D-Granular | 2.0 | |
|   | Peppermint Oil | 1.1 | Firmenich |
|   | Stepanol WA/100 (Na-Lauryl Sulfate) | 2.2 | |
| C) | Veegum HF-6% (Ag/Al Silicate) | 16.64 | |
|   | Blue #1 FD + C (0.6%) | 0.06 | |
| D) | Na—CMC 7 H 5% | 45.0 | |

The components of A were combined together and then all items of B were added to A and mixed until uniform. C was then added and mixed until uniform. Finally, D was added slowly with mixing until uniform.

Citric acid q.s. to pH 5.9 to 6.3

A and B were heated separately to 70° C. and then A was added to B. The mixture was cooled to 25° C. and then C added. pH was adjusted.

Example 25

The procedure of example 19 above was used to produce the following anti-inflammatory hand and body lotion composition for use in the method of treatment or prevention of inflammation according to the invention.

| Ingredients | % WW | Supplier |
|---|---|---|
| lauryliminodipropionic acid tocopheryl phosphate - 30% | 5.0 | VPCS |
| Sodium Ascorbyl Phosphate (SAP) 95-99% | 1.5 | BASF |
| Hydroxyethyl-Cellulose | 0.5 | HERCULES |
| Preservative Dye Deionized Water | q.s. ad 100% | |

Example 26

An anti-inflammatory facial lotion for use in the method of treatment or prevention of ultra-violet light induced erythema according to the invention was prepared as follows.

| Ingredients | % WW | Supplier |
|---|---|---|
| lauryliminodipropionic acid tocopheryl phosphate - 30% | 3.0 | VPCS |
| Sodium Ascorbyl Phosphate (SAP) 99% | 2.1 | BASF |
| Na Carboxyl Methyl Cellulose - 7 HF 5% | 35.0 | DOW |
| Preservative Dye Deionized Water | q.s. ad 100% | |

Example 27

A facial cream for use in the method of treatment or prevention of photoaging according to the invention was prepared as follows.

| Ingredients | % WW | Supplier |
|---|---|---|
| lauryliminodipropionic acid tocopheryl phosphate - 30% | 7.0 | VPCS |
| lauryliminodipropionic acid ascorbyl phosphate (LAAP) 6% | 15.0 | VPCS |
| Natrasol 250 HHR - 4% | 42.00 | |
| Preservative, Dye Fragrance DEI, | q.s. ad | |
| Deionized Water | 100% | |

Example 28

A lotion with sunscreens for use in the method of treatment or prevention of erythema and inflammation associated with sunburn according to the invention was prepared as follows.

|   | Ingredients | % WW | Supplier |
|---|---|---|---|
| A) | Brij 72 - POE 2 Stearyl Ether | 0.5 | Uniqema Americas |
|   | Emerest 132 - Stearic Acid | 2.0 | Cognis |
|   | Pelemol PDD - Propylene Glycol Dicaprylate/Dicaprate | 10.0 | Phoenix |
|   | Drake oil 9 - LT Mineral Oil | 9.0 | Penreco |
|   | Brij 721 - POE 21 Stearyl Ether | 1.0 | Uniqema Americas |
|   | Octylmethoxy Cinnamate | 7.0 | ISP |
|   | Benzophenone-3 | 2.0 | ISP |
|   | Dow Corning 200 Fluid - Dimethicone | 1.0 | Dow Corning |
|   | Propyl Paraben | 0.1 | Clariant Corp. |
| B) | Carbopol Ultrez 10 - Slurry 3% | 5.0 | B. F. Goodrich |
|   | Water Distilled | 7.5 | |
| C) | TEA - 99% | 1.2 | Union Carbide |
|   | Methyl Paraben | 0.25 | Clariant Corp. |
|   | lauryliminodipropionic acid tocopheryl phosphate - 30% | 10.0 | VPCS |
|   | Water Distilled | q.s. 100% | |

A and C were heated separately to 80° C. B was heated to 70° C. A was added to C while mixing with homogenizer 2-3 minutes. The mixture was removed from homogenizer and stirred normally whilst B was added. The product was then cooled to room temperature.

Example 29

A hand and body lotion for use in the method of treatment or prevention of erythema and inflammation associated with skin damage due to free radicals according to the invention was prepared as follows.

|   | Ingredients | % WW | Supplier |
|---|---|---|---|
| A) | Brij 72 - POE 2 Stearyl Ether | 0.5 | Uniqema Americas |
|   | Emerest 132 - Stearic Acid | 2.0 | Cognis |
|   | Pelemol PDD - Propylene Glycol Dicaprylate/Dicaprate | 10.0 | Phoenix |
|   | Drake oil 9 - LT Mineral Oil | 9.0 | Penreco |
|   | Brij 721 - POE 21 Stearyl Ether | 1.0 | Uniqema Americas |
|   | Octylethoxy Cinnamate | 5.0 | ISP |
|   | Dow Corning 200 Fluid - Dimethicone | 1.0 | Dow Corning |
|   | Propyl Paraben | 0.1 | Clariant Corp. |

-continued

| | Ingredients | % WW | Supplier |
|---|---|---|---|
| B) | Carbopol Ultrez 10 - Slurry 3% | 5.0 | B. F. Goodrich |
| | Escalol 577 | 5.0 | ISP |
| | Water Distilled | 7.5 | |
| C) | TEA - 99% | 1.2 | Union Carbide |
| | Water Distilled | 12.5 | |
| | Methyl Paraben | 0.25 | Clariant Corp. |
| | lauryliminodipropionic acid tocopheryl phosphate - 30% | 10.0 | VPCS |
| | Water Distilled | q.s. 100% | |

A and C were heated separately to 80° C. B was heated to 70° C. A was added to C while mixing with homogenizer 2-3 minutes. The mixture was removed from homogenizer and stirred normally whilst B was added. The product was then cooled to room temperature.

Example 30

A protective lotion for use in the method of treatment or prevention of erythema and inflammation associated with sunburn according to the invention was prepared as follows.

| | Ingredients | % WW | Supplier |
|---|---|---|---|
| A) | Brij 72 - POE 2 Stearyl Ether | 0.5 | Uniqema Americas |
| | Emerest 132 - Stearic Acid | 2.0 | Cognis |
| | Pelemol PDD - Propylene Glycol Dicaprylate/Dicaprate | 10.0 | Phoenix |
| | Drake oil 9 - LT Mineral Oil | 9.0 | Penreco |
| | Brij 721 - POE 21 Stearyl Ether | 1.0 | Uniqema Americas |
| | Escalol 567 | 6.0 | ISP |
| | Benzophenone-3 | 2.0 | ISP |
| | Dow Corning 200 Fluid - Dimethicone | 1.0 | Dow Corning |
| | Propyl Paraben | 0.1 | Clariant Corp. |
| B) | Carbopol Ultrez 10 - Slurry 3% | 5.0 | B. F. Goodrich |
| | Water Distilled | 7.5 | |
| C) | TEA - 99% | 1.2 | Union Carbide |
| | Water Distilled | 12.5 | |
| | Methyl Paraben | 0.25 | Clariant Corp. |
| | Lauryliminodipropionic acid tocopheryl phosphate - 30% | 10.0 | VPCS |
| | Water Distilled | q.s. 100% | |

Procedure

A and C were heated separately to 80° C. B was heated to 70° C. A was added to C while mixing with homogenizer 2-3 minutes. The mixture was removed from homogenizer and stirred normally whilst B was added. The product was then cooled to room temperature.

Example 31

A skin lotion for use in the method of treatment according to the invention was prepared as follows.

| | INGREDIENTS | % WW | SUPPLIER |
|---|---|---|---|
| A) | Brij 72 - POE 2 Stearyl Ether | 0.5 | Uniqema Americas |
| | Emerest 132 - Stearic Acid | 2.0 | Cognis |
| | Pelemol PDD - Propylene Glycol Dicaprylate/Dicaprate | 10.0 | Phoenix |
| | Drake oil 9 - LT Mineral Oil | 9.0 | Penreco |
| | Brij 721 - POE 21 Stearyl Ether | 1.0 | Uniqema Americas |
| | Escalol 587 | 5.0 | ISP |
| | Benzophenone-3 | 2.0 | ISP |
| | Dow Corning 200 Fluid - Dimethicone | 1.0 | Dow Corning |
| | Propyl Paraben | 0.1 | Clariant Corp. |

-continued

| | INGREDIENTS | % WW | SUPPLIER |
|---|---|---|---|
| B) | Carbopol Ultrez 10 - Slurry 3% | 5.0 | B. F. Goodrich |
| | Water Distilled | 7.5 | |
| C) | TEA - 99% | 1.2 | Union Carbide |
| | Water Distilled | 12.5 | |
| | Methyl Paraben | 0.25 | Clariant Corp. |
| | Lauryliminodipropionic acid tocopheryl phosphate - 30% | 10.0 | VPCS |
| | Water Distilled | q.s. 100% | |

Procedure

A and C were heated separately to 80° C. B was heated to 70° C. A was added to C while mixing with homogenizer 2-3 minutes. The mixture was removed from homogenizer and stirred normally whilst B was added. The product was then cooled to room temperature.

Example 32

An oil in water emulsion for use in the method of treatment according to the invention was prepared as follows.

| | Ingredients | % WW | Supplier |
|---|---|---|---|
| A) | Brij 72 - POE 2 Stearyl Ether | 0.5 | Uniqema Americas |
| | Emerest 132 - Stearic Acid | 2.0 | Cognis |
| | Pelemol PDD - Propylene Glycol Dicaprylate/Dicaprate | 10.0 | Phoenix |
| | Drake oil 9 - LT Mineral Oil | 9.0 | Penreco |
| | Brij 721 - POE 21 Stearyl Ether | 1.0 | Uniqema Americas |
| | Escalol 557 | 5.0 | ISP |
| | Dow Corning 200 Fluid - Dimethicone | 1.0 | Dow Corning |
| | Propyl Paraben | 0.1 | Clariant Corp. |
| B) | Carbopol Ultrez 10 - Slurry 3% | 5.0 | B. F. Goodrich |
| | Water Distilled | 7.5 | |
| C) | TEA - 99% | 1.2 | Union Carbide |
| | TiO2 | 2.0 | Tayka |
| | Water Distilled | 12.5 | |
| | Methyl Paraben | 0.25 | Clariant Corp. |
| | Lauryliminodipropionic acid tocopheryl phosphate - 30% | 10.0 | VPCS |
| | Water Distilled | q.s. 100% | |

A and C were heated separately to 80° C. B was heated to 70° C. A was added to C while mixing with homogenizer 2-3 minutes. The mixture was removed from homogenizer and stirred normally whilst B was added. The product was then cooled to room temperature.

Example 33

An oil in water emulsion for use in the method of treatment or prevention of wrinkles according to the invention was prepared as follows.

| | Ingredients | % WW | Supplier |
|---|---|---|---|
| A) | Brij 72 POE 2 - Stearyl Ether | 0.5 | Uniqema Americas |
| | Emerest 132 - Stearic Acid | 2.0 | Cognis |
| | Pelemol PDD - Propylene Glycol Dicaprylate/Dicaprate | 10.0 | Phoenix |
| | Drake oil 9 - LT Mineral Oil | 9.0 | Penreco |
| | Brij 721 - POE 21 Stearyl Ether | 1.0 | Uniqema Americas |
| | Escalol 597 | 10.0 | ISP |
| | Dow Corning 200 Fluid - Dimethicone | 1.0 | Dow Corning |
| | Propyl Paraben | 0.1 | Clariant Corp. |

-continued

| | Ingredients | % WW | Supplier |
|---|---|---|---|
| B) | Carbopol Ultrez 10 - Slurry 3% | 5.0 | B. F. Goodrich |
| | Water Distilled | 7.5 | |
| C) | TEA - 99% | 1.2 | Union Carbide |
| | Zinc Oxide | 2.0 | Z-COTE-BASF |
| | Water Distilled | 12.5 | |
| | Methyl Paraben | 0.25 | Clariant Corp. |
| | Lauryliminodipropionic acid tocopheryl phosphate - 30% | 10.0 | VPCS |
| | Water Distilled | q.s. 100% | |

A and C were heated separately to 80° C. B was heated to 70° C. A was added to C while mixing with homogenizer 2-3 minutes. The mixture was removed from homogenizer and stirred normally whilst B was added. The product was then cooled to room temperature.

Example 34

A water in oil emulsion for use in the method of treatment or prevention of aging lines according to the invention was prepared as follows.

| | Ingredients | % WW | Supplier |
|---|---|---|---|
| A) | Cetiol OE - Di-N-Octyl Ether | 23.0 | Cognis |
| | Dehymuls PGPH | 5.0 | Cognis |
| | Beeswax | 0.5 | Stahl & Pitsch |
| | Zinc Stearate | 0.5 | Whittaker |
| | Padimate O | 7.0 | ISP |
| | Avobenzone | 2.0 | |
| | Dow Corning 200 Fluid - Dimethicone | 1.0 | Dow Corning |
| B) | Magnesium Sulfate | 0.3 | |
| | Glycerin 96% | 5.0 | Dow Chemical |
| | Lauryliminodipropionic Acid Tocopheryl Phosphate - 30% | 6.67 | VPCS |
| | Sodium Ascorbyl Phosphate (SAP) - 95-99% | 1.0 | BASF |
| | Water Distilled | q.s. 100% | |
| C) | Germall II | 1.0 | Sutton Lab, ISP |

A and B were heated separately to 80° C. B was added to A while homogenizing. After emulsification, the mixture was removed from homogenizing and a propeller stirrer was used to cool down the batch. At 30° C. or 28° C., C was added and the batch was passed through a colloid mill at tight setting, cap 8-10.

Example 35

A water in oil hand and body lotion for use in the method of treatment or prevention of erythema and inflammation associated with or leading to dry rough skin according to the invention was prepared as follows.

| | Ingredients | % WW | Supplier |
|---|---|---|---|
| A) | Cetiol OE - Di-N-Octyl Ether | 23.0 | Cognis |
| | Dehymuls PGPH | 5.0 | Cognis |
| | Beeswax | 0.5 | Stahl & Pitsch |
| | Zinc Stearate | 0.5 | Whittaker |
| | Trolamine Salicylate | 7.0 | ISP |
| | Dow Corning 200 Fluid - Dimethicone | 1.0 | Dow Corning |

-continued

| | Ingredients | % WW | Supplier |
|---|---|---|---|
| B) | Magnesium Sulfate | 0.3 | |
| | MT 150 W | 5.0 | Tayca |
| | Glycerin 96% | 5.0 | Dow Chemical |
| | Lauryliminodipropionic Acid Tocopheryl Phosphate - 30% | 3.33 | VPCS |
| | Lauryliminodipropionic Acid Ascorbyl Phosphate 6% | 33.33 | VPCS |
| | Sodium Ascorbyl Phosphate (SAP) - 95-99% | 1.0 | BASF |
| | Water Distilled | q.s. 100% | |
| C) | Germall II | 1.0 | Sutton Lab, ISP |

A and B were heated separately to 80° C. B was added to A while homogenizing. After emulsification, the mixture was removed from homogenizing and a propeller stirrer was used to cool down the batch. At 30° C. or 28° C., C was added and the batch was passed through a colloid mill at tight setting, cap 8-10.

Example 36

A water in oil emulsion for skin protection for use in the method of treatment according to the invention was prepared as follows.

| | Ingredients | % WW | Supplier |
|---|---|---|---|
| A) | Cetiol OE - Di-N-Octyl Ether | 23.0 | Cognis |
| | Dehymuls PGPH | 5.0 | Cognis |
| | Beeswax | 0.5 | Stahl & Pitsch |
| | Zinc Stearate | 0.5 | Whittaker |
| | Dow Corning 200 Fluid - Dimethicone | 1.0 | Dow Corning |
| B) | Magnesium Sulfate | 0.3 | |
| | Zinc Oxide | 5.0 | Z-COTE-BASF |
| | Glycerin 96% | 5.0 | Dow Chemical |
| | Lauryliminodipropionic Acid Ascorbyl Phosphate - 6% | 10.00 | VPCS |
| | Water Distilled | q.s. 100% | |
| C) | Germall II | 1.0 | Sutton Lab, ISP |

Procedure

A and B were heated separately to 80° C. B was added to A while homogenizing. After emulsification, the mixture was removed from homogenizing and a propeller stirrer was used to cool down the batch. At 30° C. or 28° C., C was added and the batch was passed through a colloid mill at tight setting, cap 8-10.

Example 37

A water in oil emulsion for facial skin for use in the method of treatment according to the invention was prepared as follows. The ascorbyl phosphate complex provides skin lightening

| | Ingredients | % WW | Supplier |
|---|---|---|---|
| A) | Cetiol OE - Di-N-Octyl Ether | 23.0 | Cognis |
| | Dehymuls PGPH | 5.0 | Cognis |
| | Beeswax | 0.5 | Stahl & Pitsch |
| | Zinc Stearate | 0.5 | Whittaker |
| | Aminobenzoic Acid | 7.0 | ISP |
| | Homosalate | 1.0 | Witco |
| | Dow Corning 200 Fluid - Dimethicone | 1.0 | Dow Corning |

|   | Ingredients | % WW | Supplier |
|---|---|---|---|
| B) | Magnesium Sulfate | 0.3 | |
|   | Glycerin 96% | 5.0 | Dow Chemical |
|   | Lauryliminodipropionic Acid Tocopheryl Phosphate - 30% | 5.0 | VPCS |
|   | Lauryliminodipropionic Acid Ascorbyl Phosphate - 30% | 5.0 | VPCS |
|   | Water Distilled | q.s. 100% | |
| C) | Germall II | 1.0 | Sutton Lab, ISP |

A and B were heated separately to 80° C. B was added to A while homogenizing. After emulsification, the mixture was removed from homogenizing and a propeller stirrer was used to cool down the batch. At 30° C. or 28° C., C was added and the batch was passed through a colloid mill at tight setting, cap 8-10.

Example 38

A water in oil emulsion for sun protection for use in the method of treatment or prevention of erythema and inflammation associated with most common skin conditions including eczema according to the invention was prepared as follows.

|   | Ingredients | % WW | Supplier |
|---|---|---|---|
| A) | Cetiol OE - Di-N-Octyl Ether | 23.0 | Cognis |
|   | Dehymuls PGPH | 5.0 | Cognis |
|   | Beeswax | 0.5 | Stahl & Pitsch |
|   | Zinc Stearate | 0.5 | Whittaker |
|   | Phenylbenzimidazole Sulfonic Acid | 7.0 | ISP |
|   | Cinoxate | 2.0 | ISP |
|   | Dow Corning 200 Fluid - Dimethicone | 1.0 | Dow Corning |
| B) | Magnesium Sulfate | 0.3 | |
|   | Glycerin 96% | 5.0 | Dow Chemical |
|   | Lauryliminodipropionic Acid Tocopheryl Phosphate and Lauryliminodipropionic Acid Ascorbyl Phosphate - 30% | 10.0 | VPCS |
|   | Water Distilled | 44.7 | |
| C) | Germall II | 1.0 | Sutton Lab, ISP |

A and B were heated separately to 80° C. B was added to A while homogenizing. After emulsification, the mixture was removed from homogenizing and a propeller stirrer was used to cool down the batch. At 30° C. or 28° C., C was added and the batch was passed through a colloid mill at tight setting, cap 8-10.

Example 39

A water in oil emulsion for use in the method of promoting healthy skin according to the invention was prepared as follows.

|   | Ingredients | % WW | Supplier |
|---|---|---|---|
| A) | Cetiol OE Di-N-Octyl Ether | 23.0 | Cognis |
|   | Dehymuls PGPH | 5.0 | Cognis |
|   | Beeswax | 0.5 | Stahl & Pitsch |
|   | Zinc Stearate | 0.5 | Whittaker |
|   | Padimate O | 7.0 | ISP |
|   | Dioxybenzone | 2.0 | ISP |
|   | Dow Corning 200 Fluid - Dimethicone | 1.0 | Dow Corning |
| B) | Magnesium Sulfate | 0.3 | |
|   | Glycerin 96% | 5.0 | Dow Chemical |
|   | Lauryliminodipropionic Acid Tocopheryl Phosphate - 30% | 10.0 | VPCS |
|   | Water Distilled | 44.7 | |
| C) | Germall II | 1.0 | Sutton Lab, ISP |

A and B were heated separately to 80° C. B was added to A while homogenizing. After emulsification, the mixture was removed from homogenizing and a propeller stirrer was used to cool down the batch. At 30° C. or 28° C., C was added and the batch was passed through a colloid mill at tight setting, cap 8-10.

Example 40

A water in oil emulsion for total body protection for use in the method of treatment or prevention of erythema and inflammation associated with rosacea according to the invention was prepared as follows.

|   | Ingredients | % WW | Supplier |
|---|---|---|---|
| A) | Cetiol OE - Di-N-Octyl Ether | 23.0 | Cognis |
|   | Dehymuls PGPH | 5.0 | Cognis |
|   | Beeswax | 0.5 | Stahl & Pitsch |
|   | Zinc Stearate | 0.5 | Whittaker |
|   | Octyl Methoxy Cinnamate | 7.0 | ISP |
|   | Methyl Anthranilate | 2.0 | |
|   | Dow Corning 200 Fluid - Dimethicone | 1.0 | Dow Corning |
| B) | Magnesium Sulfate | 0.3 | |
|   | Glycerin 96% | 5.0 | Dow Chemical |
|   | Lauryliminodipropionic Acid Tocopheryl Phosphate - 30% | 10.0 | VPCS |
|   | Water Distilled | 44.7 | |
| C) | Germall II | 1.0 | Sutton Lab, ISP |

A and B were heated separately to 80° C. B was added to A while homogenizing. After emulsification, the mixture was removed from homogenizing and a propeller stirrer was used to cool down the batch. At 30° C. or 28° C., C was added and the batch was passed through a colloid mill at tight setting, cap 8-10.

Example 41

A sunscreen with silicone for use in the method of preventing or treating erythema and inflammation associated with sunburn according to the invention was prepared as follows.

| Ingredients | % WW | Supplier |
|---|---|---|
| Polyglycerol-4 Isostearic Acid and Cetyl Dimethicone Copolyol and Hexyl Laurate | 10.00 | BASF |
| Cremophor GS32 | 0.60 | |
| Glyceryl Tribehenate | 3.00 | |
| Cetyl Methicone | 2.00 | |
| $C_{12}$-$C_{15}$ Alkyl Benzoate | 5.00 | |
| Cyclomethicone | 8.85 | Dow Corning |
| Z Cote HP-1 - Zinc Oxide and Dimethicone | 5.00 | BASF |
| Phenyl Trimethicone | 7.00 | Dow Corning |
| Uvinol TiO2 | 3.00 | BASF |
| Xanthan Gum | 0.10 | |
| Glycerin | 3.00 | |

-continued

| Ingredients | % WW | Supplier |
|---|---|---|
| Deionized Water | q.s. 100% | |
| Disodium EDTA | 0.10 | Dow Corning |
| Lauryliminodipropionic Acid Tocopheryl Phosphate - 30% | 3.33 | VPCS |
| Lauryliminodipropionic Acid Ascorbyl Phosphate - 30% | 6.67 | VPCS |
| Fragrance Preservative | q.s. | |

Example 42

A protective shampoo and conditioner for use in the method of treatment according to the invention was prepared as follows.

| Ingredients | % WW | Supplier |
|---|---|---|
| Sodium Lauryl (1) Ether Sulfate | 5.00 | |
| Cocamidopropyl Betaine | 1.50 | |
| Merquat 550 | 5.00 | |
| Cocamide MEA | 2.00 | |
| Cinnamidopropyl trimonnium chloride(catc) | 4.00 | |
| Lauryliminodipropionic Acid Tocopheryl Phosphate - 30% | 2.00 | VPCS |
| Fragrance Preservative | q.s. as desired | |
| Deionized Water | q.s. ad 100% | |

Adjust pH to 6.0-6.5 with citric acid.

Example 43

A protective rinse-off hair conditioner for use in the method of treatment or prevention of erythema and inflammation associated with dandruff according to the invention was prepared as follows:

| Ingredients | % WW | Supplier |
|---|---|---|
| Distearyl Dimethyl Ammonium Chloride | 2.0 | |
| Brij 721 - POE 21 Stearyl Ether | 1.0 | Uniqema Americas |
| Stearyl Alcohol | 1.0 | |
| Lauryliminodipropionic Acid Tocopheryl Phosphate and Lauryliminodipropionic Acid Ascorbyl Phosphate - 30% | 2.0 | VPCS |
| Fragrance, Preservative | q.s. as desired | |
| Deionized Water | q.s. ad 100% | |

Example 44

A protective spray for hair and skin for use in the method of treatment or prevention of erythema and inflammation associated with dandruff was prepared as follows.

| Ingredients | % WW | Supplier |
|---|---|---|
| Uvinol MS-40 | 2.00 | BASF |
| Masil SF 19 | 1.00 | BASF |
| DL Panthenol | 2.00 | BASF |
| Lauryliminodipropionic Acid Tocopheryl Phosphate - 30% | 3.00 | VPCS |

| Ingredients | % WW | Supplier |
|---|---|---|
| Peg 40 Castor Oil | 0.50 | BASF |
| Citric Acid | q.s. as desired | |
| Preservative, Fragrance | q.s. as desired | |
| Ethanol/Water 50/50 | q.s. ad 100% | |

Pharmaceutical Composition Example 45

Aqueous gel composition for use in the method of treatment according to the invention was prepared according to the following formulation:

| Ingredient | W/w percent |
|---|---|
| Oleyliminipentanoic acid retinyl phosphates | 15 |
| Carbomer.RTM. 940 | 1 |
| sodium hydroxide to desired pH | QS |
| water | QS |

Example 46

A cream for use in the methods according to the invention was prepared as follows according to the procedure in Example 4:

| | W/W |
|---|---|
| PHASE A | |
| Deionized water | 59.00% |
| Glycerol | 5.00 |
| Arginine as free base | 1.74 |
| Trisodium EDTA | 0.05 |
| Carbomer (Carbopol Ultrez 10)[2] | 0.50 |
| Lauryliminodipropionic Acid Ubiquinyl Phosphate[1] | 8.64 |
| PHASE B | |
| Cetearyl Alcohol (and) Ceteareth-20 (Phoenoxol T)[3] | 2.00 |
| Glyceryl Stearate (Emerest 2400)[4] | 1.00 |
| Isopropyl Myristate (Pelemol IPM)[3] | 5.00 |
| Cetyl Ethylhexanoate (Pelemol 168)[3] | 3.50 |
| Isocetyl Behenate (Pelemol ICB)[3] | 3.50 |
| Oleyl Erucate (Cetiol J-600)[4] | 3.00 |
| Dimethicone (Dow 200,100 cSt.)[5] | 0.50 |
| PHASE C | |
| Deionized Water | 5.00 |
| Triethanolamine (99%) | 0.50 |
| PHASE D | |
| Propylene Glycol (and) Diazolidinyl Urea (and) Methylparaben (and) Propylparaben (Germaben II)[6] | 1.00 |
| | 100.00% |

Example 47

A cream for use in the methods according to the invention was prepared as follows according to the procedure in Example 4:

|  | W/W |
|---|---|
| PHASE A | |
| Deionized water | 65.00% |
| Glycerol | 5.00 |
| Trisodium EDTA | 0.05 |
| Arginine as free base | 1.74 |
| Carbomer (Carbopol Ultrez.10)[2] | 0.50 |
| Lauryliminodipropionic Acid Ascorbyl Phosphate[1] | 2.60 |
| PHASE B | |
| Cetearyl Alcohol (and) Ceteareth-20 (Phoenoxol T)[3] | 2.00 |
| Glyceryl Stearate (Emerest 2400)[4] | 1.00 |
| Isopropyl Myristate (Pelemol IPM)[3] | 5.00 |
| Cetyl Ethylhexanoate (Pelemol 168)[3] | 3.50 |
| Isocetyl Behenate (Pelemol ICB)[3] | 3.50 |
| Oleyl Erucate (Cetiol J-600)[4] | 3.00 |
| Dimethicone (Dow 200,100 cSt.)[5] | 0.50 |
| PHASE C | |
| Deionized Water | 5.00 |
| Triethanolamine (99%) | 0.50 |
| PHASE D | |
| Propylene Glycol (and) Diazolidinyl Urea (and) Methylparaben (and) Propylparaben (Germaben II)[6] | 1.00 |
| | 100.00% |

Pharmaceutical Composition Example 48

Aqueous gel composition for use in the method of treatment according to the invention was prepared according to the following formulation:

| Ingredient | W/w percent |
|---|---|
| Tocotrienol phosphate histadine complexes | 15 |
| retin A | 0.5 |
| Carbomer.RTM. 940 | 1 |
| sodium hydroxide to desired pH | QS |
| water | QS |

Pharmaceutical Composition Example 49

Aqueous gel composition for use in the method of treatment according to the invention was prepared according to the following formulation:

| Ingredient | W/w percent |
|---|---|
| palmyliminodiproprionic acid P: tocopheryl P: ascorbyl phosphate diesters | 15 |
| retin A | 0.5 |
| Carbomer.RTM. 940 | 1 |
| sodium hydroxide to desired pH | QS |
| water | QS |

Summary

The examples above illustrate that the method of the invention provides treatment and preventative properties for skin conditions.

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

The invention claimed is:

1. A method for treating a skin condition comprising topically administering a composition comprising an effective skin-penetrating amount of a lauryliminodipropionic acid tocopheryl phosphate complex.

2. The method according to claim 1 wherein the composition additionally comprises a topically acceptable carrier.

3. The method according to claim 1 wherein the skin condition is selected from the group consisting of deterioration of skin homeostasis, inflammation, erythema, wound, burn, sun sensitivity, dandruff, rosacea, dermatitis, gingivitis, sunburn, heat burn, psoriasis, insect bites, seborrheic dermatitis, calluses, corns, eczema, photo-aging, wrinkles, common warts, plantar warts, thickening of the epidermal layer and pigmentation.

4. The method according to claim 1 wherein the composition comprises 0.01 to 30% by weight (of the total composition) of the complex.

5. The method according to claim 4 wherein the composition comprises 1 to 15% by weight (of the total composition) of the complex.

6. The method according to claim 5 wherein the composition comprises 1 to 5% by weight (of the total composition) of the complex.

7. The method according to claim 6 wherein the composition comprises 1 to 3% by weight (of the total composition) of the complex.

8. The method according to claim 1 wherein the composition additionally comprises at least one other active ingredient selected from the group consisting of antibiotics, antihistamines, disinfectants, antiseptics, salicylic acid, retinoic acid, anti-inflammatories, keratolytic agents, sunscreens, and mixtures thereof.

9. The method according to claim 8 wherein the topical formulation further comprises an effective antimicrobial amount of one or more antibiotics.

10. The method according to claim 9 wherein the antibiotic is selected from the group consisting of erythromycin, lincomycin family, cephalosporins, tetracycline family, and combinations thereof.

11. The method according to claim 9 wherein the antibiotic is present in an amount of 0.01 to 5.0% by weight of the total composition.

12. The method according to claim 8 wherein the topical formulation further comprises a keratolytic agent.

13. The method according to claim 12 wherein the keratolytic agent is present in an amount of 0.1 to 6.0% by weight of the total composition.

14. The method according to claim 13 wherein the keratolytic agent is present in an amount of 0.5 to 3.0% by weight of the total composition.

15. The method according to claim 8 wherein the composition additionally comprises salicylic acid or retinoic acid.

16. The method according to claim 15 wherein the composition additionally comprises retinoic acid.

17. A method according to claim 8 wherein the topical formulation further comprises one or more physical or chemical sunscreens.

18. A method according to claim 3 wherein the skin condition is acne.

19. A method according to claim 18 which further comprises administering a keratolytic agent subsequently to or simultaneously with the administration of the lauryliminodipropionic acid tocopheryl phosphate complex.

20. A method according to claim 18 wherein said acne involves a bacterial infection and wherein said method further comprises administering an antibiotic subsequently to or simultaneously with the administration of the lauryliminodipropionic acid tocopheryl phosphate complex.

21. A method according to claim 20 wherein said antibiotic administration is topical.

22. A method according to claim 20 wherein said antibiotic administration is oral.

23. A method according to claim 18 which further comprises administering an antiseptic subsequently to or simultaneously with the administration of the lauryliminodipropionic acid tocopheryl phosphate complex.

24. A method according to claim 18 wherein the pharmaceutical formulation comprises: (a) 1 to 10% by weight of the total composition of lauryliminodipropionic acid tocopheryl phosphate; (b) 0.1 to 10% by weight of the total composition of Carbomer ultrez 3%; (c) 0.1 to 10% by weight of the total composition of triethanolamine; (d) optional colouring agents and preservatives; and (e) balance of the total composition of water.

25. The method according to claim 24 comprising about 3% (w/w) lauryliminodipropionic acid tocopheryl phosphate.

26. A method according to claim 3 wherein the skin condition is sunburn.

27. The method according to claim 26 wherein the pharmaceutical formulation comprises about 1 to 3% (w/w) lauryliminodipropionic acid tocopheryl phosphate.

28. A method according to claim 3 wherein the skin condition is roscaea.

29. The method according to claim 28 wherein the pharmaceutical formulation comprises about 1 to 3% (w/w) lauryliminodipropionic acid tocopheryl phosphate.

30. A method according to claim 3 wherein the skin condition is an insect bite or sting.

31. The method according to claim 30 wherein the pharmaceutical formulation comprises about 1 to 3% (w/w) lauryliminodipropionic acid tocopheryl phosphate.

32. A method according to claim 3 wherein the skin condition is a heat burn.

33. The method according to claim 32 wherein the pharmaceutical formulation comprises about 1 to 3% (w/w) lauryliminodipropionic acid tocopheryl phosphate.

34. A method according to claim 3 wherein the skin condition is dermatitis.

35. The method according to claim 34 wherein the pharmaceutical formulation comprises about 1 to 3% (w/w) lauryliminodipropionic acid tocopheryl phosphate.

36. A method according to claim 3 wherein the skin condition is sebhorratic dermatitis.

37. The method according to claim 36 wherein the pharmaceutical formulation comprises about 1 to 3% (w/w) lauryliminodipropionic acid tocopheryl phosphate.

38. A method according to claim 3 wherein the skin condition is photo-aging.

39. The method according to claim 38 wherein the pharmaceutical formulation comprises about 1 to 3% (w/w) lauryliminodipropionic acid tocopheryl phosphate.

40. A method according to claim 3 wherein the skin condition is wrinkles.

41. The method according to claim 40 wherein the pharmaceutical formulation comprises about 1 to 3% (w/w) lauryliminodipropionic acid tocopheryl phosphate.

42. A method according to claim 3 wherein the skin condition is pigmentation.

43. The method according to claim 42 wherein the pharmaceutical formulation comprises about 1 to 3% (w/w) lauryliminodipropionic acid tocopheryl phosphate.

44. A method for treating a skin condition comprising topically administering a composition comprising: (a) 0.1 to 10% by weight of the total composition of lauryliminodipropionic acid tocopheryl phosphate; (b) 0.1 to 10% by weight of the total composition of glycerin; (c) 0.01 to 5% by weight of the total composition of trisodium EDTA; (d) 0.01 to 5% by weight of the total composition of carbomer (Carbopol Ultrez 10); (e) 0.1 to 10% by weight of the total composition of cetearyl alcohol (and) Ceteareth-20 (Phoenoxol T); (f) 0.1 to 5% by weight of the total composition of glyceryl stearate; (g) 0.1 to 10% by weight of the total composition of isopropyl myristate; (h) 0.1 to 10% by weight of the total composition of cetyl ethylhexanoate; (i) 0.1 to 10% by weight of the total composition of isocetyl behenate; (j) 0.1 to 10% by weight of the total composition of oleyl erucate; (k) 0.01 to 5% by weight of the total composition of dimethicone; (l) 0.01 to 5% by weight of the total composition of triethanolamine; (m) 0.1 to 10% by weight of the total composition of propylene glycol, diazolidinyl urea, methylparaben, and propylparaben (Germaben II); and (n) balance of the total composition of water.

* * * * *

UNITED STATES PATENT AND TRADEMARK OFFICE
CERTIFICATE OF CORRECTION

PATENT NO.        : 8,008,345 B2                                  Page 1 of 1
APPLICATION NO.   : 10/485196
DATED             : August 30, 2011
INVENTOR(S)       : Simon Michael West et al.

It is certified that error appears in the above-identified patent and that said Letters Patent is hereby corrected as shown below:

Title Page, Item (60), replace the filling date of [[Jul. 26, 2002]] with --Jul. 27, 2011-- for provisional application No. 60/308,496

Signed and Sealed this
Sixth Day of December, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,008,345 B2 | Page 1 of 1 |
| APPLICATION NO. | : 10/485196 | |
| DATED | : August 30, 2011 | |
| INVENTOR(S) | : Simon Michael West et al. | |

It is certified that error appears in the above-identified patent and that said Letters Patent is hereby corrected as shown below:

Title Page, Item (60), replace the filing date of [[Jul. 26, 2002]] with --Jul. 27, 2001-- for provisional application No. 60/308,496

This certificate supersedes the Certificate of Correction issued December 6, 2011.

Signed and Sealed this
Sixth Day of March, 2012

David J. Kappos
*Director of the United States Patent and Trademark Office*